United States Patent
Finley et al.

(10) Patent No.: US 12,059,221 B2
(45) Date of Patent: *Aug. 13, 2024

(54) MOTION PROGRAMMING OF A ROBOTIC DEVICE

(71) Applicant: NuVasive, Inc., San Diego, CA (US)

(72) Inventors: Eric Finley, San Diego, CA (US); James Grotting, San Diego, CA (US)

(73) Assignee: Nuvasive, Inc., San Diego, CA (US)

( * ) Notice: Subject to any disclaimer, the term of this patent is extended or adjusted under 35 U.S.C. 154(b) by 293 days.

This patent is subject to a terminal disclaimer.

(21) Appl. No.: 17/550,318

(22) Filed: Dec. 14, 2021

(65) Prior Publication Data

US 2022/0096180 A1    Mar. 31, 2022

Related U.S. Application Data

(63) Continuation of application No. 16/544,915, filed on Aug. 20, 2019, now Pat. No. 11,229,493.

(60) Provisional application No. 62/794,545, filed on Jan. 18, 2019.

(51) Int. Cl.
*A61B 34/30* (2016.01)
*A61B 34/10* (2016.01)
*A61B 34/20* (2016.01)

(52) U.S. Cl.
CPC ............. *A61B 34/30* (2016.02); *A61B 34/10* (2016.02); *A61B 34/20* (2016.02); *A61B 2034/107* (2016.02); *A61B 2034/2065* (2016.02)

(58) Field of Classification Search
CPC ......... A61B 34/30; A61B 34/10; A61B 34/20; A61B 2034/107; A61B 2034/2065; A61B 2034/2055; A61B 2090/376
See application file for complete search history.

(56) References Cited

U.S. PATENT DOCUMENTS

| | | |
|---|---|---|
| 9,125,680 B2 | 9/2015 | Kostrzewski |
| 9,283,048 B2 | 3/2016 | Kostrzewski |
| 9,308,050 B2 | 4/2016 | Kostrzewski |
| 9,833,292 B2 | 12/2017 | Kostrzewski |

(Continued)

FOREIGN PATENT DOCUMENTS

| | | |
|---|---|---|
| JP | 2012-533333 | 12/2012 |
| WO | 2015/135055 | 9/2015 |

OTHER PUBLICATIONS

PCT International Search Report and Written Opinion in International Application PCT/US2020/014131, mailed May 7, 2020, 14 pages.

(Continued)

*Primary Examiner* — Joel Lamprecht

(57) ABSTRACT

A method comprising acquiring an image of a surgical site of a patient. The method includes capturing motion data of an instrument based on a user defined path to the surgical site. The method includes determining a motion path based on the captured motion data. The motion path corresponds to an actuation of one or more components of a robotic device. The method includes displaying a portion of the motion path onto the image. The method includes determining one or more instructions for actuating the one or more components along the determined motion path. The method includes providing the one or more instructions to the robotic device.

20 Claims, 10 Drawing Sheets

(56) References Cited

U.S. PATENT DOCUMENTS

| | | |
|---|---|---|
| 10,034,716 B2 | 7/2018 | Crawford |
| 10,058,394 B2 | 8/2018 | Johnson |
| 10,624,710 B2 | 4/2020 | Crawford |
| 10,646,298 B2 | 5/2020 | Johnson |
| 10,660,712 B2 | 5/2020 | Kostrzewski |
| 10,675,094 B2 | 6/2020 | Crawford |
| 10,828,120 B2 | 11/2020 | Kostrzewski |
| 10,874,466 B2 | 12/2020 | Crawford |
| 10,925,681 B2 | 2/2021 | Johnson |
| 11,039,893 B2 | 6/2021 | Kostrzewski |
| 11,058,504 B2 | 7/2021 | Blanco |
| 11,065,065 B2 | 7/2021 | Rezach |
| 11,229,493 B2 * | 1/2022 | Finley ............... A61B 34/30 |
| 2015/0366624 A1 | 12/2015 | Kostrzewski |
| 2016/0074123 A1 | 3/2016 | Bly |
| 2017/0076501 A1 | 3/2017 | Jagga |
| 2018/0286135 A1 | 10/2018 | Jagga |
| 2020/0069377 A1 | 3/2020 | Finley |

OTHER PUBLICATIONS

PCT International Preliminary Report on Patentability in International Application PCT/US2020/014131, mailed Jul. 29, 2021, 10 pages.

Japanese Office Action in Application 2021-541237, mailed Aug. 23, 2022, pages.

* cited by examiner

MOTION PROGRAMMING OF A ROBOTIC DEVICE

CROSS-REFERENCE TO RELATED APPLICATION

This application is a continuation of U.S. patent application Ser. No. 16/544,915, filed Aug. 20, 2019, which claims the benefit of and priority to U.S. Provisional Application No. 62/794,545, filed on Jan. 18, 2019. The entire disclosure of these priority applications is incorporated herein by reference in the entirety for any and all purposes.

FIELD

This disclosure describes motion programming of a robotic device based on a tracked surgical instrument.

BACKGROUND

Minimally invasive surgery typically limits the size of incisions into a human body so that the recovery from surgical procedures may be quick and the odds of infection reduced. However, only a few tools may be concurrently used by the same surgeon during minimally invasive surgery. Sometimes a tool change may occur to place the proper tool with the surgical suite. A tool change may extend out of time of a minimally invasive surgical procedure. Moreover, minimally invasive surgery may be burdensome on a surgeon, particularly when manually operating surgical controls for long periods of time.

SUMMARY

In one embodiment, a method includes acquiring an image of a surgical site of a patient. The method also includes capturing motion data of an instrument based on a user defined path to the surgical site. The method also includes determining a motion path based on the captured motion data. The motion path corresponds to an actuation of one or more components of a robotic device. The method also includes displaying a portion of the motion path onto the image. The method also includes determining one or more instructions for actuating the one or more components along the determined motion path. The method also includes providing the one or more instructions to the robotic device.

In another embodiment, a method includes acquiring an image of a surgical site of a patient. The method also includes capturing a pose of an instrument based on a user defined placement of the instrument at a surgical site of a patient. The method also includes determining a motion path corresponding to the captured pose of the instrument. The motion path is associated with actuation of one or more components of a robotic device. The method also includes displaying a portion of the motion path onto the merged image. The method also includes determining one or more instructions for actuating the one or more components along the determined motion path. The method also includes providing the one or more instructions to the robotic device.

In another embodiment, a system includes a tracking device, a robotic device, and a processing device. The processing device includes a processor and a non-transitory computer readable medium. The non-transitory computer readable medium includes stored instructions that, when executed by the processor, cause the system to acquire an image of a surgical site of a patient. The stored instructions also cause the system to capture, via the tracking device, a pose of an instrument based on a user defined placement of the instrument at a surgical site of a patient. The stored instructions also cause the system to determine, by the processor, a motion path corresponding to the captured pose of the instrument. The motion path is associated with actuation of one or more components of the robotic device. The stored instructions also cause the system to provide instructions to display a portion of the motion path onto the image. The stored instructions also cause the system to determine, by the processor, one or more instructions for actuating the one or more components along the determined motion path. The stored instructions also cause the system to provide the one or more instructions to the robotic device.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION

Figure 1:
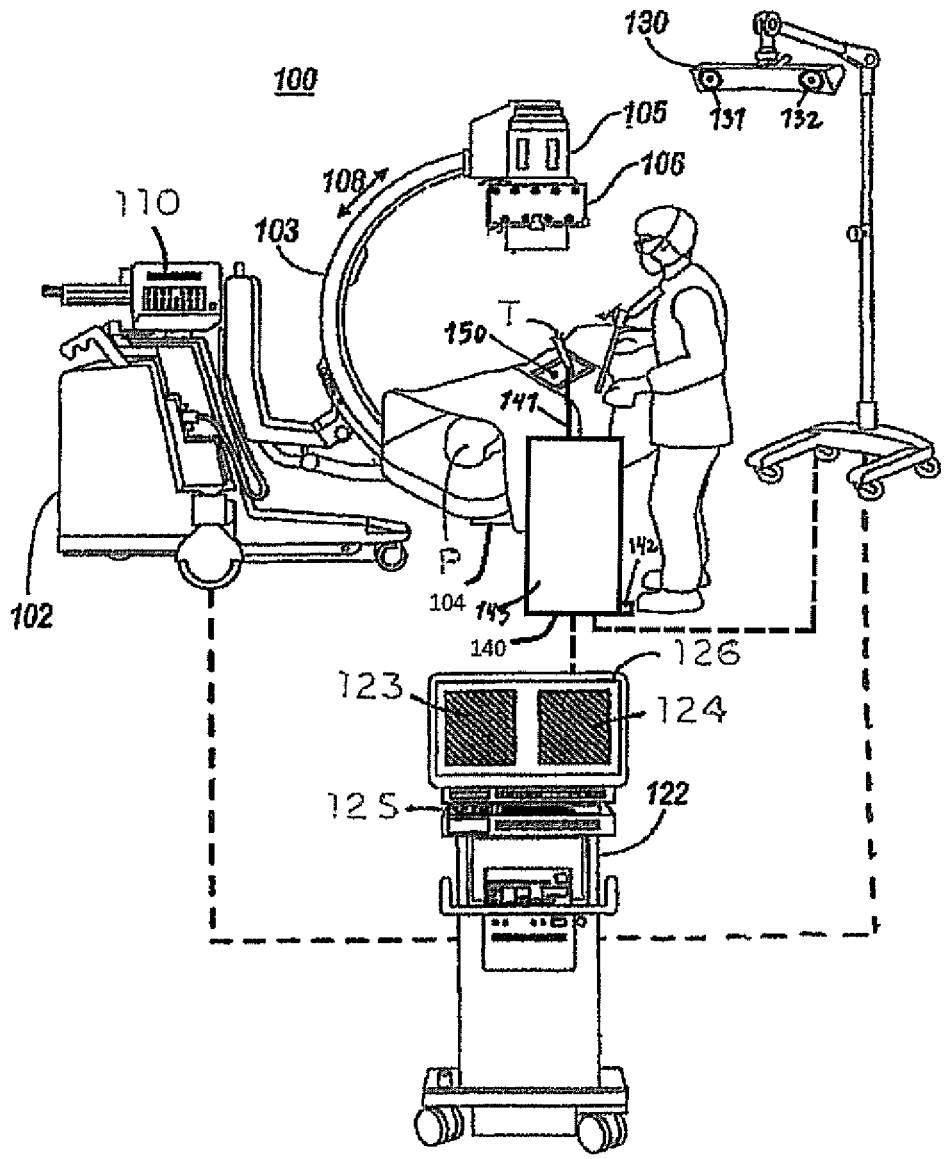
FIG. 1 illustrates an example system for performing a surgical procedure, according to an embodiment of the present disclosure.

Illustrative embodiments of the invention are described below. In the interest of clarity, not all features of an actual implementation are described in this specification. It will of course be appreciated that in the development of any such actual embodiment, numerous implementation-specific decisions must be made to active the developers' specific goals, such as compliance with system-related and business-related constraints, which will vary from one implementation to another. Moreover, it will be appreciated that such a development effort might be complex and time-consuming, but nevertheless be a routine undertaking for those of ordinary skill in the art having the benefit of this disclosure. It is furthermore to be readily understood that, although discussed below primarily within the context of spinal surgery, the systems and methods of the present invention may be employed in any number of anatomical settings to provide access to any number of different surgical target sites throughout the body.

Examples described herein include systems and methods for performing a surgical procedure. In one example, a method includes acquiring an image of a surgical site of a patient. In another example, a method includes acquiring a high resolution baseline image of a surgical site of a patient. In one example, the high resolution baseline image is an X-ray image captured via a mobile fluoroscopy machine. Continuing with this example, a processing device is configured to digitally manipulate the high resolution baseline image to produce a baseline image set based on adjusting one or more aspects of the high resolution baseline image. The method also includes acquiring a new image of the surgical site at lower resolution than the high resolution baseline image.

In one example, the lower resolution image is an X-ray image that is captured at a radiation level that is lower than the radiation level associated with the high resolution baseline image. Due to the image quality of the lower resolution image, the processing device is configured to find a match between the lower resolution image and an image from the high resolution baseline image set by comparing the lower resolution image to one or more images of the baseline image set. The processing device is configured to select a representative image of the baseline image set having an acceptable degree of correlation with the lower resolution image. The processing device is also configured to merge the selected representative image with the lower resolution image to produce a merged image. In one embodiment, the merged image is displayed on a display for a user (e.g., a surgeon) to assess one or more aspects of the surgical procedure.

The method also includes capturing motion data of an instrument used by the surgeon based on a user defined path to the surgical site. The processing device is configured to determine a motion path based on the captured motion data. The motion path corresponds to an actuation of one or more components of a robotic device that will assist a surgeon in completing the surgical procedure. The method also includes displaying a portion of the motion path onto the merged image for the surgeon to review.

For example, in a surgical procedure involving the use of one or more pedicle screws, a surgeon may position an instrument at a pedicle target site and view a motion path corresponding to the insertion of a pedicle screw based on the captured motion data of the instrument. In this example, the surgeon may select a point on the pedicle target site and pivot the instrument to see one or more different trajectories overlaid onto the merged image. Based on the instrument being pivoted about the point, one or more tracking devices are configured to capture the motion data associated with the movements of the instrument. This motion data is then processed accordingly as described herein and at least a portion of the motion path is overlaid onto the merged image. The surgeon may provide an input (e.g., a voice command, accessing an interface, etc.) to the processing device as to whether the motion path is in alignment with a preoperative plan. Based on approval of the motion path, the method includes determining one or more instructions for actuating the one or more components of the robotic device along the determined motion path. The method also includes providing the one or more instructions to the robotic device.

Referring now to the figures, FIG. 1 is a diagram of an example system 100 for performing a surgical procedure. The example system 100 includes a base unit 102 supporting a C-Arm imaging device 103. The C-Arm 103 includes a radiation source 104 that is positioned beneath the patient P and that directs a radiation beam upward to the receiver 105. The receiver 105 of the C-Arm 103 transmits image data to a processing device 122. The processing device 122 may communicate with a tracking device 130 to obtain position and orientation information of various instruments T and H used during the surgical procedure. The tracking device 130 may communicate with a robotic device 140 to provide location information of various tracking elements, such as marker 150. The robotic device 140 and the processing device 122 may communicate via one or more communication channels.

The base unit 102 includes a control panel 110 through which a user can control the location of the C-Arm 103, as well as the radiation exposure. The control panel 110 thus permits the radiology technician to "shoot a picture" of the surgical site at a surgeon's direction, control the radiation dose, and initiate a radiation pulse image.

The C-Arm 103 may be rotated about the patient P in the direction of the arrow 108 for different viewing angles of the surgical site. In some instances, implants or instruments T and H may be situated at the surgical site, necessitating a change in viewing angle for an unobstructed view of the site. Thus, the position of the receiver relative to the patient P, and more particularly relative to the surgical site of interest, may change during a procedure as needed by the surgeon or radiologist. Consequently, the receiver 105 may include a tracking target 106 mounted thereto that allows tracking of the position of the C-Arm 103 using the tracking device 130. By way of example only, the tracking target 106 may include a plurality of infrared (IR) reflectors or emitters spaced around the target, while the tracking device 130 is configured to triangulate the position of the receiver 105 from the IR signals reflected or emitted by the tracking target 106.

The processing device 122 can include a digital memory associated therewith and a processor for executing digital and software instructions. The processing device 122 may also incorporate a frame grabber that uses frame grabber technology to create a digital image for projection as displays 123 and 124 on a display device 126. The displays 123 and 124 are positioned for interactive viewing by the surgeon during the procedure. The two displays 123 and 124 may be used to show images from two views, such as lateral and A/P, or may show a baseline scan and a current scan of the surgical site, or a current scan and a "merged" scan based on a prior baseline scan and a low radiation current scan, as described herein. An input device 125, such as a keyboard or a touch screen, can allow the surgeon to select and manipulate the on-screen images. It is understood that the input device may incorporate an array of keys or touch screen icons corresponding to the various tasks and features implemented by the processing device 122. The processing device 122 includes a processor that converts the image data obtained from the receiver 105 into a digital format. In some cases, the C-Arm 103 may be operating in the cinematic exposure mode and generating many images each second. In these cases, multiple images can be averaged together over a short time period into a single image to reduce motion artifacts and noise.

The tracking device 130 includes sensors 131 and 132 for determining location data associated with a variety of elements (e.g., an infrared reflector or emitter) used in a surgical procedure. In one example, the sensors 131 and 132 may be a charge-coupled device (CCD) image sensor. In another example, the sensors 131 and 132 may be a complementary metal-oxide-semiconductor (CMOS) image sensor. It is also envisioned that a different number of other image sensors may be used to achieve the functionality described.

In one aspect of the present invention, the robotic device 140 may assist with holding an instrument T relative to the patient P during a surgical procedure. In one scenario, the robotic device 140 may be configured to maintain the instrument T in a relative position to the patient P as the patient P moves (e.g., due to breathing) or is moved (e.g., due to manipulation of the patient's body) during the surgical procedure.

The robotic device 140 may include a robot arm 141, a pedal 142, and a mobile housing 143. The robotic device 140 may also be in communication with a display such as display 126. The robotic device 140 may also include a fixation device to fix the robotic device 140 to an operating table.

In one example, in a first tracking mode, the tracking device 130 is configured to capture motion data of a handheld instrument based on a user defined path at a surgical target site of the patient. In this example, the processing device 122 determines a motion path corresponding to the captured motion data. Further, the processing device 122 determines one or more instructions for actuating the one or more components of the robotic device 140 along the determined motion path and provides the one or more instructions to the robotic device 140. In a second tracking mode, the tracking device 130 is configured to capture the pose (i.e., the orientation and position) of a handheld instrument based on a user defined placement of the instrument at a surgical site of the patient. In this example, the processing device 122 determines a motion path corresponding to the captured pose of the instrument. As described with the first tracking mode, the processing device 122 determines one or more instructions for actuating the one more components of the robotic device 140 along the determined motion and provides the one or more instructions to the robotic device 140.

In one example, a user may control actuation of the robot arm 141 through the use of a robot pedal 142. In one embodiment, the user may depress the robot pedal 142 to activate one or more modes of the robotic device 140. In one scenario, the user may depress the robot pedal 142 to allow the user to manually position the robot arm 141 according to a desired position. In another scenario, the user may depress the robot pedal 142 to activate a mode that enables the robot arm 141 to place an instrument T in a position according to a determined motion path as described above. In another scenario, the user may depress the robot pedal 142 to stop the robot arm 141 from proceeding with any further movements.

The robot arm 141 may be configured to receive one or more end effectors depending on the surgical procedure and the number of associated joints. In one example, the robot arm 141 may be a six joint arm. In this example, each joint includes an encoder which measures its angular value. The movement data provided by the one or more encoders, combined with the known geometry of the six joints, may allow for the determination of the position of the robot arm 141 and the position of the instrument T coupled to the robot arm 141. It also envisioned that a different number of joints may be used to achieve the functionality described herein.

The mobile housing 143 ensures easy handling of the robotic device 140 through the use of wheels or handles or both. In one embodiment, the mobile housing 143 may include immobilization pads or an equivalent device. The mobile housing 143 may also include a control unit which provides one or more commands to the robot arm 141 and allows a surgeon to manually input data through the use of an interface, such as a touch screen, a mouse, a joystick, a keyboard or similar device.

In one example, the processing device 122 is configured to capture a pose of an instrument H (e.g., a portable instrument) via the tracking device 130. The captured pose of the instrument includes a combination of position information and orientation information. In this example, the pose of the instrument H is based on a user defined placement at a surgical site of the patient P. The user defined placement is based on movement of the instrument H by a surgeon. In one scenario, the portable instrument comprises one or more infrared reflectors or emitters. Continuing with this example, the processing device 122 is configured to determine a motion path corresponding to the captured pose of the instrument H. The motion path is associated with the actuation of one or more components (e.g., one or more links and joints) of the robotic device 140. The processing device 122 is configured to determine one or more instructions for actuating the one or more components of the robotic device 140 along the determined motion path. Further, the processing device 122 is configured to provide the one or more instructions to the robotic device 140.

In another example, the processing device 122 is configured to compare a position of the one or more infrared reflectors of the portable instrument to a position of one or more infrared reflectors coupled to the patient. Based on the comparison, the processing 122 is configured to determine whether a distance between the one or more infrared reflectors of the portable instrument and the one or more infrared reflectors coupled to the patient is within a safety threshold. Based on the determination of the distance between the portable instrument and the patient, the processing device 122 is configured to determine one or more adjustments to the actuation of the one or more components of the robotic device.

In another example, the processing device 122 is configured to provide an image of the surgical site for display on display device 126. In this example, the processing device 122 is configured to overlay at least a portion of the determined motion path onto the image of the surgical site. Overlaying at least a portion of the determined path would allow a surgeon to review the path and ensure that it aligns with a surgical operative plan. In one example, the processing device 122 may be further configured to receive an input from the surgeon confirming that the overlaid portion of the determined motion path aligns with the surgical operative plan. In one example, the input is received through input device 125.

In another example, the processing device 122 is configured to determine an angle between a preoperative trajectory and the trajectory corresponding to the portion of the motion path. Based on the determined angle, the processing device 122 is configured to determine one or more movements to pivot an instrument based on the captured position of the instrument H in order to align the trajectory corresponding to the portion of the motion path and the preoperative trajectory. In this example, the processing device 122 is configured to provide the one or more movements to pivot the instrument to the robotic device 140. The robotic device 140, as described herein, is configured to convert the one or more movements to pivot into instructions for enabling movement of the robotic device 140 along a determined trajectory.

In another example, the determined angle between the preoperative trajectory and the trajectory corresponding to the portion of the motion path may be compared to one or more ranges associated with one or more scores. Based on the score, a varying visual effect (e.g., a blinking color) may be displayed with the trajectory corresponding to the portion of the motion path. For example, if the angle is within a range associated with a higher likelihood of breaching a perimeter of the pedicle, then the trajectory corresponding to the portion of the motion path is displayed in a blinking red color. In another example, if the angle is within a range corresponding to a high degree of correlation to the preoperative trajectory, then the trajectory corresponding to the portion of the motion path is displayed in a green color.

In another example, the processing device 122 is configured to determine that the overlaid portion of the determined motion path intersects with one or more predetermined boundaries within the surgical site. In this example, the processing device 122 is configured to provide for display a varying visual effect of the overlaid at least a portion of the determined motion path via the display device 126.

Figure 2:
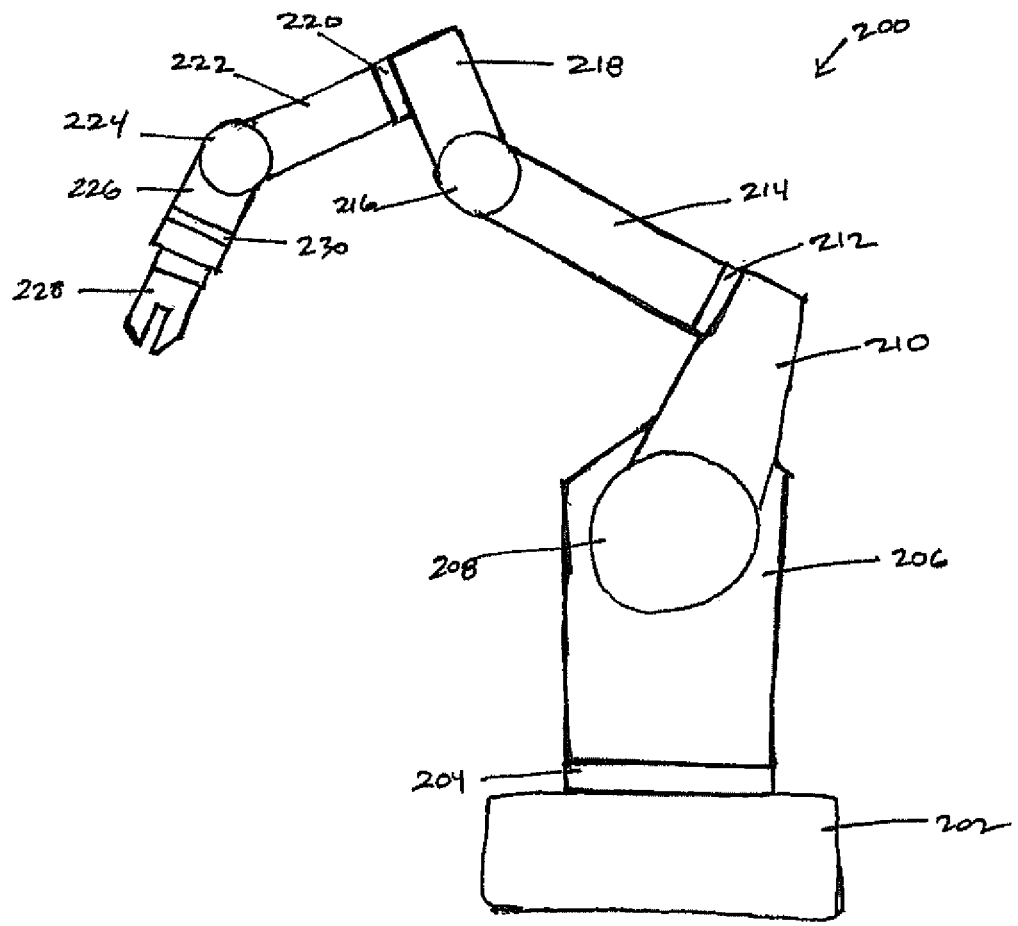
FIG. 2 illustrates an example robotic device that may be used during a surgical procedure, according to an embodiment of the present disclosure.

FIG. 2 illustrates an example robotic device 200 that may be used during a surgical procedure. The robotic device 200 may contain hardware, such as a processor, memory or storage, and sensors that enable the robotic device 200 for use in a surgical procedure. The robotic device 200 may be powered by various means such as electric motor, pneumatic motors, hydraulic motors, etc. The robotic device 200 includes a base 202, links 206, 210, 214, 218, 222, and 226, joints 204, 208, 212, 216, 220, 224, and 230, and manipulator 228.

The base 202 may provide a platform in order to provide support for the robotic device 200. The base 202 may be stationary or coupled to wheels in order to provide movement of the robotic device 200. The base 202 may comprise any number of materials such as aluminum, steel, stainless steel, etc., that may be suitable for a given environment associated with the robotic device 200.

The links 206, 210, 214, 218, 222, and 226 may be configured to be moved according to a programmable set of instructions. For instance, the links may be configured to follow a predetermined set of movements (e.g., a motion path corresponding to a captured pose of an instrument) in order to accomplish a task under the supervision of a user. By way of example, the links 206, 210, 214, 218, 222, and 226 may form a kinematic chain that defines relative movement of a given link of links 206, 210, 214, 218, 222, and 226 at a given joint of the joints 204, 208, 212, 216, 220, 224, and 230.

The joints 204, 208, 212, 216, 220, 224, and 230 may be configured to rotate through the use of a mechanical gear system. In one example, the mechanical gear system is driven by a strain wave gearing, a cycloid drive, etc. The mechanical gear system selected would depend on a number of factors related to the operation of the robotic device 200 such as the length of the given link of the links 206, 210, 214, 218, 222, and 226, speed of rotation, desired gear reduction, etc. Providing power to the joints 204, 208, 212, 216, 220, 224, and 230 will allow for the links 206, 210, 214, 218, 222, and 226 to be moved in a way that allows the manipulator 228 to interact with an environment.

In one example, the manipulator 228 is configured to allow the robotic device 200 to interact with the environment according to one or more constraints. In one example, the manipulator 228 performs appropriate placement of an element through various operations such as gripping a surgical instrument. By way of example, the manipulator 228 may be exchanged for another end effector that would provide the robotic device 200 with different functionality.

In one example, the robotic device 200 is configured to operate according to a robot operating system (e.g., an operating system designed for specific functions of the robot). A robot operating system may provide libraries and tools (e.g., hardware abstraction, device drivers, visualizers, message-passing, package management, etc.) to enable robot applications.

Figure 3:
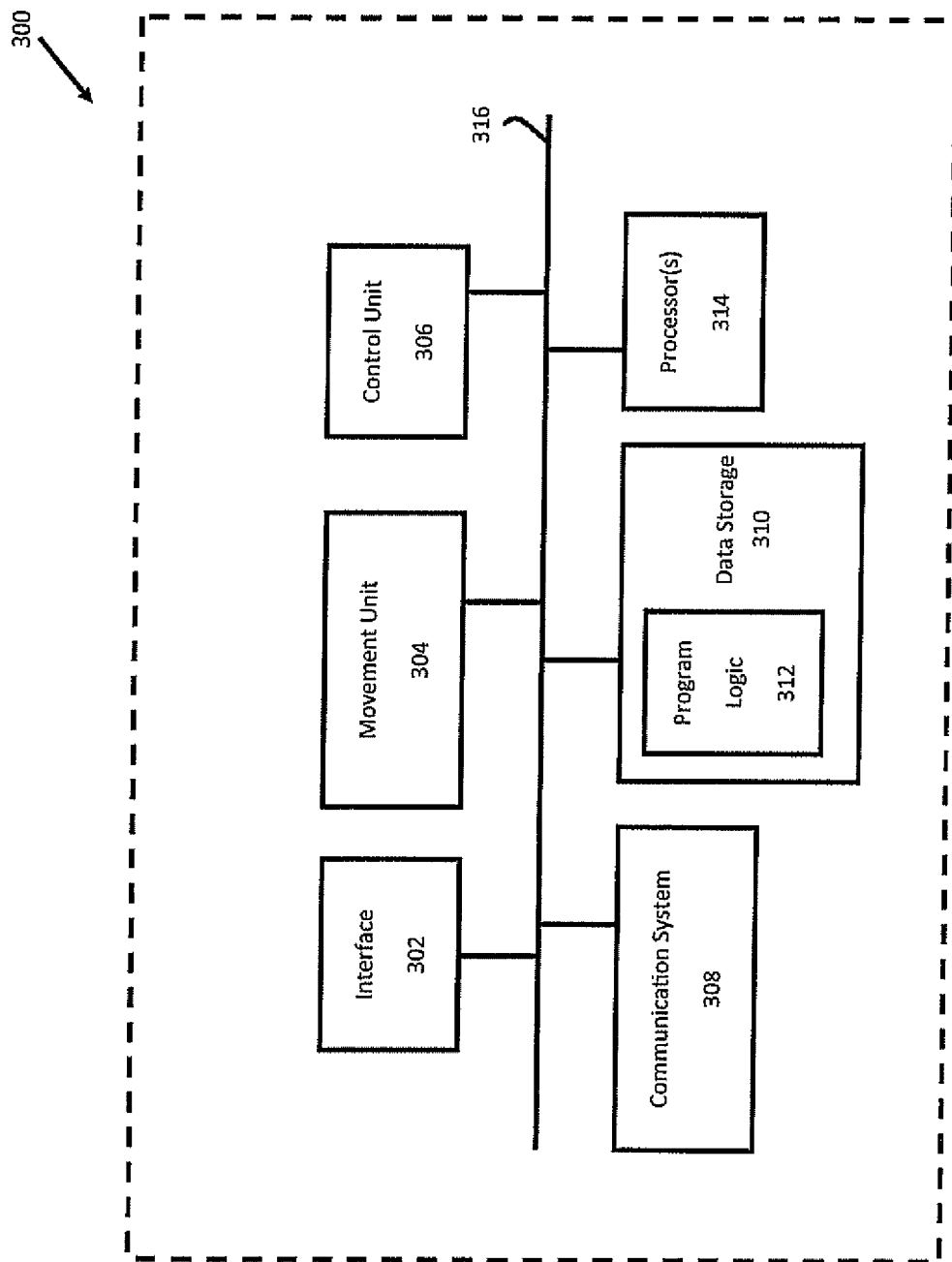
FIG. 3 illustrates an example block diagram of a computing device, according to an embodiment of the present disclosure.

FIG. 3 is a block diagram of a computing device 300, according to an example embodiment. In some examples, some components illustrated in FIG. 3 may be distributed across multiple computing devices (e.g., desktop computers, servers, hand-held devices, etc.). However, for the sake of the example, the components are shown and described as part of one example device. The computing device 300 may include an interface 302, a movement unit 304, a control unit 306, a communication system 308, a data storage 310, and a processor 314. Components illustrated in FIG. 3 may be linked together by a communication link 316. In some examples, the computing device 300 may include hardware to enable communication within the computing device 300 and another computing device (not shown). In one embodiment, the robotic device 140 or the robotic device 200 may include the computing device 300.

The interface 302 may be configured to allow the computing device 300 to communicate with another computing device (not shown). Thus, the interface 302 may be configured to receive input data from one or more devices. In some examples, the interface 302 may also maintain and manage records of data received and sent by the computing device 300. In other examples, records of data may be maintained and managed by other components of the computing device 300. The interface 302 may also include a receiver and transmitter to receive and send data. In some examples, the interface 302 may also include a user-interface, such as a keyboard, microphone, touch screen, etc., to receive inputs as well. Further, in some examples, the interface 302 may also interface with output devices such as a display, speaker, etc.

In one example, the interface 302 may receive an input indicative of location information corresponding to one or more elements of an environment in which a robotic device (e.g., robotic device 140, robotic device 200) resides. In this example, the environment may be an operating room in a hospital comprising a robotic device configured to function during a surgical procedure. The interface 302 may also be configured to receive information associated with the robotic device. For instance, the information associated with the robotic device may include operational characteristics of the robotic device and a range of motion with one or more components (e.g., joints 204, 208, 212, 216, 220, 224, and 230) of the robotic device (e.g., robotic device 140, robotic device 200).

The control unit 306 of the computing device 300 may be configured to run control software which exchanges data with components (e.g., robot arm 141, robot pedal 142, joints 204, 208, 212, 216, 220, 224, and 230, manipulator 228, etc.) of a robotic device (e.g., robotic device 140, robotic device 200) and one or more other devices (e.g., processing device 122, tracking device 130, etc.). The control software may communicate with a user through a user interface and display monitor (e.g., display 126) in communication with the robotic device. The control software may also communicate with the tracking device 130 and the processing device 122 through a wired communication interface (e.g., parallel port, USB, etc.) and/or a wireless communication interface (e.g., antenna, transceivers, etc.). The control software may communicate with one or more sensors to measure the efforts exerted by the user at the instrument T mounted to a robot arm (e.g., robot arm 141, link 226). The control software may communicate with the robot arm to control the position of the robot arm relative to the marker 150.

As described above, the control software may be in communication with the tracking device 130. In one scenario, the tracking device 130 may be configured to track the marker 150 that is attached to the patient P. By way of example, the marker 150 may be attached to a spinous process of a vertebra of the patient P. In this example, the marker 150 may include one or more infrared reflectors that are visible to the tracking device 130 to determine the location of the marker 150. In another example, multiple markers may be attached to one or more vertebrae and used to determine the location of the instrument T.

In one example, the tracking device 130 may provide updates in near real-time of the location information of the marker 150 to the control software of the robotic device 140. The robotic device 140 may be configured to receive updates to the location information of the marker 150 from the tracking device 130 via a wired and/or wireless interface. Based on the received updates to the location information of the marker 150, the robotic device 140 may be configured to determine one or more adjustments to a first position of the instrument T in order to maintain a desired position of the instrument T relative to the patient P.

In one embodiment, the control software may include independent modules. In an exemplary embodiment, these independent modules run simultaneously under a real time environment and use a shared memory to ensure management of the various tasks of the control software. The modules may have different priorities, such as a safety module having the highest priority, for example. The safety module may monitor the status of the robotic device 140. In one scenario, the safety module may send an instruction to the control unit 306 to stop the robot arm 141 when a critical situation is detected, such as an emergency stop, software failure, or collision with an obstacle, for example.

In one example, the interface 302 is configured to allow the robotic device 140 to communicate with other devices (e.g., processing device 122, tracking device 130). Thus, the interface 302 is configured to receive input data from one or more devices. In some examples, the interface 302 may also maintain and manage records of data received and sent by other devices. In other examples, the interface 302 may use a receiver and transmitter to receive and send data.

The interface 302 may be configured to manage the communication between a user and control software through a user interface and display screen (e.g., via displays 123 and 124). The display screen may display a graphical interface that guides the user through the different modes associated with the robotic device 140. The user interface may enable the user to control movement of the robot arm 141 associated with the beginning of a surgical procedure, activate a tracking mode to be used during a surgical procedure, and stop the robot arm 141 if needed, for example.

The movement unit 304 may be configured to determine the movement associated with one or more components of the robot arm 141 to perform a given procedure. In one embodiment, the movement unit 304 may be configured to determine the trajectory of the robot arm 141 using forward and inverse kinematics. In one scenario, the movement unit 304 may access one or more software libraries to determine the trajectory of the robot arm 141. In another example, the movement unit 304 is configured to receive one or more instructions for actuating the one or more components of the robotic device 140 from the processing device 122 according to the captured motion data of an instrument based on a user defined path.

The movement unit 304 may be configured to simulate an operation of the robotic device 140 moving an instrument T along a given path. In one example, based on the simulated operation, the movement unit 304 may determine a metric associated with the instrument T. Further, the movement unit 304 may be configured to determine a force associated with the metric according to the simulated operation. In one example, the movement unit 304 may contain instructions that determine the force based on an open kinematic chain.

The movement unit 304 may include a force module to monitor the forces and torques measured by one or more sensors coupled to the robot arm 141. In one scenario, the force module may be able to detect a collision with an obstacle and alert the safety module.

The control unit 306 may be configured to manage the functions associated with various components (e.g., robot arm 141, pedal 142, etc.) of the robotic device 140. For example, the control unit 306 may send one or more commands to maintain a desired position of the robot arm 141 relative to the marker 150. The control unit 306 may be configured to receive movement data from a movement unit 304.

In one scenario, the control unit 306 can instruct the robot arm 141 to function according to a cooperative mode. In the cooperative mode, a user is able to move the robot arm 141 manually by holding the tool T coupled to the robot arm 141 and moving the instrument T to a desired position. In one example, the robotic device 140 may include one or more force sensors coupled to an end effector of the robot arm 141. By way of example, when the user grabs the instrument T and begins to move it in a direction, the control unit 306 receives efforts measured by the force sensor and combines them with the position of the robot arm 141 to generate the movement desired by the user.

In one scenario, the control unit 306 can instruct the robot arm 141 to function according to a given mode that will cause the robotic device 140 to maintain a relative position of the instrument T to a given IR reflector or emitters (e.g., the marker 150). In one example, the robotic device 140 may receive updated position information of the marker 150 from the tracking device 130 and adjust as necessary. In this example, the movement unit 304 may determine, based on the received updated position information of the marker 150, which joint(s) of the robot arm 141 need to move in order to maintain the relative position of the instrument T with the marker 150.

In another scenario, a restrictive cooperative mode may be defined by a user to restrict movements of the robotic device 140. For the example, the control unit 306 may restrict movements of the robot arm 141 to a plane or an axis, according to user preference. In another example, the robotic device 140 may receive information pertaining to one or more predetermined boundaries within the surgical site that should not intersect with a portion of a determined motion path.

In one embodiment, the robotic device 140 may be in communication with the processing device 122. In one example, the robotic device 140 may provide the position and orientation data of the instrument T to the processing device 122. In this example, the processing device 122 may be configured to store the position and orientation data of the instrument T for further processing. In one scenario, the image processing device 122 may use the received position and orientation data of the instrument T to overlay a virtual representation of the instrument T on display 126.

In one embodiment, a sensor configured to detect a pressure or force may be coupled to the last joint of the robot arm (e.g., link 226). Based on a given movement of the robot arm, the sensor may provide a reading of the pressure exerted on the last joint of the robot arm to a computing device (e.g., a control unit of the robotic device). In one example, the robotic device may be configured to communicate the force or pressure data to a computing device (e.g., processing device 122). In another embodiment, the sensor may be coupled to an instrument such as a retractor. In this embodiment, the force or pressure exerted on the retractor and detected by the sensor may be provided to the robotic device (e.g., robotic device 140, robotic device 200) or a computing device (e.g., processing device 122) or both for further analysis.

In one scenario, the robotic device may access movement data stored in a memory of the robotic device to retrace a movement along a determined motion path. In one example, the robotic device may be configured to move the surgical tool along the determined motion path to reach or move away from the surgical site.

In another aspect, a robotic device (e.g., robotic device 140, robotic device 200) may assist with movement of an instrument along the determined motion path. In one scenario, the surgeon may plan for a trajectory of a pedicle screw intra-operatively by holding a portable instrument (e.g., instrument H) at a position outside the skin and seeing how the trajectory intersects the anatomy of concern by overlaying at least a portion of the determined motion path onto an image of the surgical site. In one example, the robotic device may be configured to move along a different trajectory until the tool intersects with a pedicle screw trajectory captured via the portable instrument. In this example, the robotic device may provide a signal to a computing device (e.g., processing device 122, computing device 300) which in turn could notify the surgeon via an audible or visual alert that the ideal pedicle screw trajectory has been reached.

In another scenario, once the instrument coupled to a robot arm (e.g., robot arm 141, links 206, 210, 214, 218, 222, and 226) of a robotic device reaches a desired pedicle screw trajectory, the robotic device may be configured to receive an input from the surgeon to travel along the desired pedicle screw trajectory. In one example, the surgeon may provide an input to the robotic device (e.g., depressing the pedal 142) to confirm the surgeon's decision to enable the robotic device to travel along the desired pedicle screw trajectory. In another example, a user may provide another form of input to either the robotic device or the computing device to assist with movement of an instrument along a determined motion path.

In one scenario, once the robotic device has received confirmation to travel along the desired pedicle screw trajectory, the robotic device may receive instructions from the movement unit 304 to pivot from the current trajectory to the desired pedicle screw trajectory. The movement unit 304 may provide the control unit 306 the required movement data to enable the robotic device to move along the desired pedicle screw trajectory.

In another aspect of the present invention, a robotic device (e.g., robotic device 140, robotic device 200) may be configured to pivot about an area of significance based on the captured pose of a portable instrument (e.g., instrument H). For example, the robotic device may be configured to pivot a retractor about the tip of the retractor so that all the steps associated with retraction of soft tissue do not need to be repeated. In one example, the movement unit 304 may determine the trajectory required to pivot the retractor.

In one example, the robotic device may be coupled to a retractor that is holding soft tissue away from a surgical site. In this example, a surgeon may need to slightly reposition the retractor due to a patient movement. To do so, the surgeon may activate a mode on the robotic device that causes the retractor to pivot by moving the robot arm (e.g., robot arm 141, links 206, 210, 214, 218, 222, and 226) according to a trajectory determined by the movement unit 304. In one example, a user may input the direction and amount of movement desired via a computing device (e.g., the processing device 122, computing device 300). After the direction and amount of movement have been entered, the user (e.g., a surgeon) may interface with the robotic device (e.g., depress the pedal 142) to begin the movement of the instrument coupled to the robot arm. In one example, the robotic device may allow a user to view a different aspect of the anatomy without disengaging from a docking point.

In another example, the movement unit 304 may provide one or more trajectories based on the captured pose of the portable instrument (e.g., instrument H) to a computing device (e.g., processing device 122) for display on display 126. In this example, a user may choose from one or more predetermined movements associated with a given procedure. For example, a given predetermined movement may be associated with a specific direction and amount of movement to be performed through the use of depressing the pedal 142 of the robotic device 140.

In another aspect of the present invention, one or more infrared (IR) reflectors or emitters may be coupled to a robot arm (e.g., robot arm 141, links 206, 210, 214, 218, 222, and 226) of the robotic device (e.g., robotic device 140, robotic device 200). In one scenario, the tracking device 130 may be configured to determine the location of the one or more IR reflectors or emitters prior to beginning operation of the robotic device. In this scenario, the tracking device 130 may provide the location information of the one or more IR reflectors or emitters to a computing device (e.g., processing device 122, computing device 300) for further processing.

In one example, the processing device 122 or computing device 300 may be configured to compare the location information of the one or more IR reflectors or emitters coupled to the robot arm with data stored on a local or remote database that contains information about the robotic device (e.g., a geometric model of the robotic device) to assist in determining a location or position of the robot arm. In one example, the processing device 122 may determine a first position of the robot arm from information provided by the tracking device 130. In this example, the processing device 122 may provide the determined first position of the robot arm to the robotic device or a computing device (e.g., computing device 300). In one example, the robotic device may use the received first position data to perform a calibration of one or more elements (e.g., encoders, actuators) associated with the one or more joints of the robot arm.

In one scenario, an instrument coupled to the robot arm of the robotic device may be used to determine a difference between an expected tip location of the instrument and the actual tip location of the instrument. In this scenario, the robotic device may proceed to move the instrument to a known location by the tracking device 130 so that the tip of the tool is in contact with the known location. The tracking device 130 may capture the location information corresponding to the one or more IR reflectors or emitters coupled to the robot arm and provide that information to the robotic device or a computing device (e.g., processing device 122, computing device 300). Further, either the robotic device or the computing device may be configured to adjust a coordinate system offset between the robotic device and the tracking device 130 based on the an expected tip location of the tool and the actual tip location of the tool.

In another aspect, a force or pressure sensor may be coupled to a robot arm (e.g., robot arm 141, links 206, 210, 214, 218, 222, and 226) of a robotic device (e.g., robotic device 140, robotic device 200). In one example, the force or pressure sensor may be located on an end effector of the robot arm. In another example, the force or pressure sensor may be coupled to a given joint of the robotic arm. The force or pressure sensor may be configured to determine when a force or pressure reading is above a resting threshold. The resting threshold may be based on a force or pressure experienced at the sensor when the end effector is holding the instrument without any additional forces or pressure applied to the instrument (e.g., a user attempting to move the instrument). In one example, the robot arm may stop moving if the force or pressure reading is at or below the resting threshold.

In one example, the movement of the robot arm 141 may be controlled by depression of the pedal 142. For example, while the pedal 142 is depressed, the control unit 306 and the movement unit 304 may be configured to receive any measures of force or pressure from the one or more force sensors and used the received information to determine the trajectory of the robot arm 141.

In another example, the movement of the robot arm 141 may be regulated by how much the pedal 142 is depressed. For example, if the user depresses the pedal 142 to the full amount, the robot arm 141 may move with a higher speed compared to when the pedal 142 is depressed at half the amount. In another example, the movement of the robot arm 141 may be controlled by a user interface located on the robotic device.

In one example, the robotic device (e.g., robotic device 140, robotic device 200) may be configured to store, in a local or remote memory, movement data that corresponds to a user defined motion path based on movement of a portable instrument. In this example, the robotic device may be configured to travel in one or more directions along a trajectory corresponding to the stored movement data. For example, a surgeon may instruct the robotic device to reverse along the trajectory corresponding to the stored movement data.

In another aspect of the present invention, a robotic device (e.g., robotic device 140, robotic device 200) may be used to navigate one or more surgical instruments and provide the navigation information to a computing device (e.g., processing device 122, computing device 300) for further processing. In one example, the computing device may be configured to determine a virtual representation of the surgical instrument. Further, the computing device may be configured to overlay the virtual representation of the surgical instrument on a two-dimensional or three-dimensional image of the surgical site.

In one example, the robotic device may perform a calibration procedure between the tracking device 130 in order to remove the dependence on the tracking device 130 for location information in the event that a line of sight between the robotic device and the tracking device 130 is blocked. In one example, using a robotic device which has been registered to a navigation system, as described herein, and a patient's three-dimensional image that corresponds to the surgical site may allow the robotic device to become independent of the degradation of accuracy with distance associated with the tracking device 130.

The communication system 308 may include a wired communication interface (e.g., parallel port, USB, etc.) and/or a wireless communication interface (e.g., antenna, transceivers, etc.) to receive and/or provide signals from/to external devices. In some examples, the communication system 308 may receive instructions for operation of the processing device 122. Additionally or alternatively, in some examples, the communication system 308 may provide output data.

The data storage 310 may store program logic 312 that can be accessed and executed by the processor(s) 314. The program logic 312 may contain instructions that provide control to one or more components of the processing device 122, the robotic device 140, the robotic device 200, etc. For example, program logic 312 may provide instructions that adjust the operation of the robotic device 200 based one on or more user defined trajectories associated with a portable instrument. The data storage 310 may comprise one or more volatile and/or one or more non-volatile storage components, such as optical, magnetic, and/or organic storage, and the data storage may be integrated in whole or in part with the processor(s) 314.

The processor(s) 314 may comprise one or more general-purpose processors and/or one or more special-purpose processors. To the extent the processor 314 includes more than one processor, such processors may work separately or in combination. For example, a first processor may be configured to operate the movement unit 304, and a second processor of the processors 314 may operate the control unit 306.

Still further, while each of the components are shown to be integrated in the processing device 122, robotic device 140, or robotic device 200, in some embodiments, one or more components may be removably mounted to otherwise connected (e.g., mechanically or electrically) to the processing device 122, robotic device 140, or robotic device 200 using wired or wireless connections.

Figure 4:
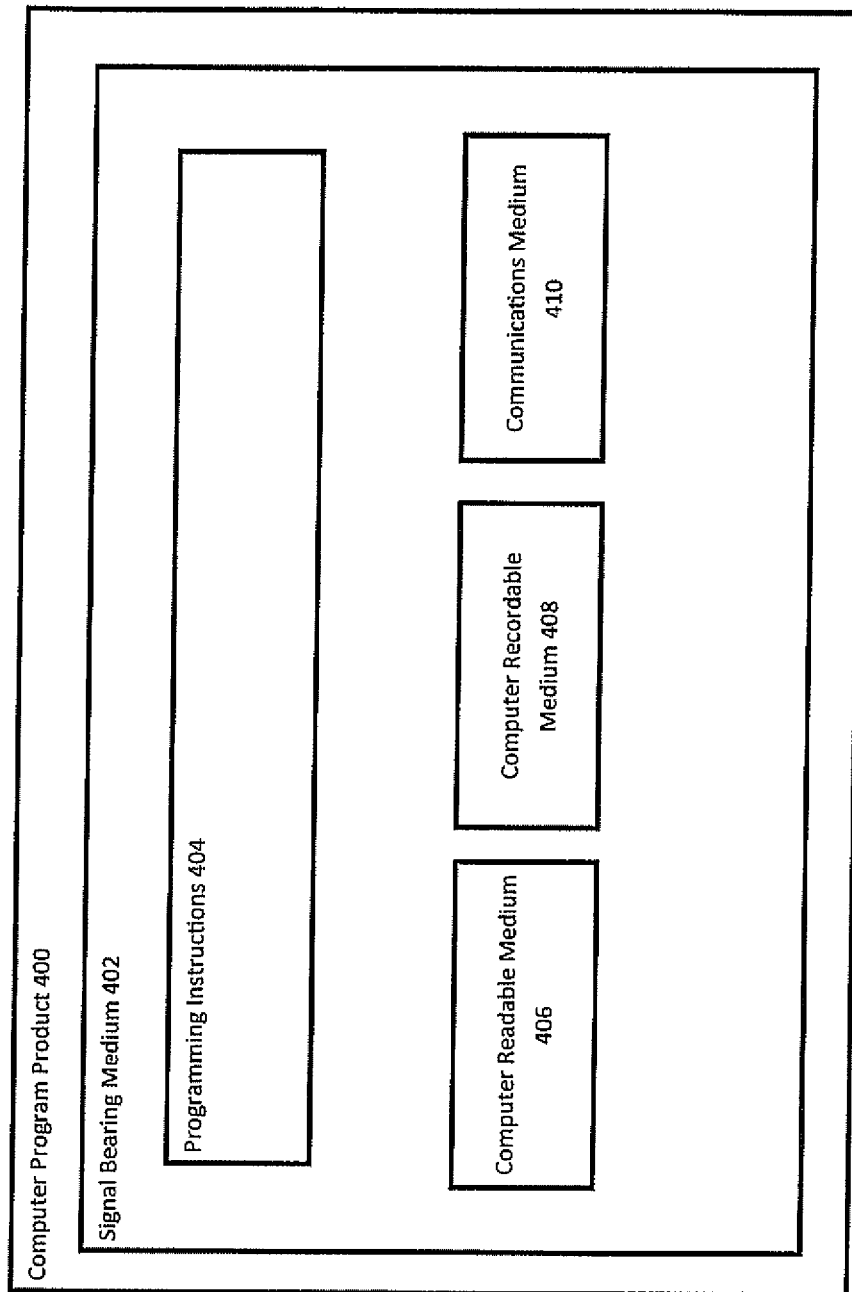
FIG. 4 illustrates an example computer medium, according to an embodiment of the present disclosure.

FIG. 4 depicts an example computer readable medium configured according to an example embodiment. In example embodiments, an example system may include one or more processors, one or more forms of memory, one or more input devices/interfaces, one or more output devices/interfaces, and machine readable instructions that when executed by the one or more processors cause the system to carry out the various functions tasks, capabilities, etc., described above.

As noted above, in some embodiments, the disclosed techniques (e.g., functions of the robotic device 140, robotic device 200, processing device 122, computing device 300, etc.) may be implemented by computer program instructions encoded on a computer readable storage media in a machine-readable format, or on other media or articles of manufacture. FIG. 4 is a schematic illustrating a conceptual partial view of an example computer program product that includes a computer program for executing a computer process on a computing device, arranged according to at least some embodiments disclosed herein.

In one embodiment, an example computer program product 400 is provided using a signal bearing medium 402. The signal bearing medium 402 may include one or more programming instructions 404 that, when executed by one or more processors, may provide functionality or portions of the functionality described above with respect to FIGS. 1-3. In some examples, the signal bearing medium 402 may be a computer-readable medium 406, such as, but not limited to, a hard disk drive, a Compact Disc (CD), a Digital Video Disk (DVD), a digital tape, memory, etc. In some implementations, the signal bearing medium 402 may be a computer recordable medium 408, such as, but not limited to, memory, read/write (R/W) CDs, R/W DVDs, etc. In some implementations, the signal bearing medium 402 may be a communication medium 410 (e.g., a fiber optic cable, a waveguide, a wired communications link, etc.). Thus, for example, the signal bearing medium 402 may be conveyed by a wireless form of the communications medium 410.

The one or more programming instructions 404 may be, for example, computer executable and/or logic implemented instructions. In some examples, a computing device may be configured to provide various operations, functions, or actions in response to the programming instructions 404 conveyed to the computing device by one or more of the computer readable medium 406, the computer recordable medium 408, and/or the communications medium 410.

The computer readable medium 406 may also be distributed among multiple data storage elements, which could be remotely located from each other. The computing device that executes some or all of the stored instructions could be an external computer, or a mobile computing platform, such as a smartphone, tablet device, personal computer, wearable device, etc. Alternatively, the computing device that executes some or all of the stored instructions could be remotely located computer system, such as a server.

FIGS. 5, 6, 9, and 10 are flow diagrams of example methods during a surgical procedure, in accordance with at least one or more embodiments described herein. Although the blocks in each figure are illustrated in a sequential order, the blocks may in some instances be performed in parallel, and/or in a different order than those described therein. Also, the various blocks may be combined into fewer blocks, divided into additional blocks, and/or removed based upon the desired implementation.

In addition, the flow diagram of FIGS. 5, 6, 9, and 10 shows the functionality and operation of possible implementations of the present embodiment. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. The computer readable medium may include non-transitory computer-readable media that stores data for short periods of time, such as register memory, processor cache, or Random Access Memory (RAM), and/or persistent longterm storage, such as read only memory (ROM), optical or magnetic disks, or compact-disc read only memory (CD-ROM), for example. The computer readable media may be able, or include, any other volatile or non-volatile storage systems. The computer readable medium may be considered a computer readable storage medium, a tangible storage device, or other article of manufacture, for example.

Alternatively, each block in FIGS. 5, 6, 9, and 10 may represent circuitry that is wired to perform the specific logical functions in the process. Illustrative methods, such as those shown in FIGS. 5, 6, 9, and 10, may be carried out in whole in or in part by a component or components in the cloud and/or system 100 of FIG. 1. However, it should be understood that the example methods may instead be carried out by other entities or combinations of entities (i.e., by other computing devices and/or combination of computer devices), without departing from the scope of the invention. For example, functions of the methods of FIGS. 5, 6, 9, and 10 may be fully performed by a computing device (or components of a computing device such as one or more processors), or may be distributed across multiple components of the computing device, across multiple computing devices (e.g., control unit 118 and image processing device 122 of FIG. 1), and/or across a server.

Figure 5:
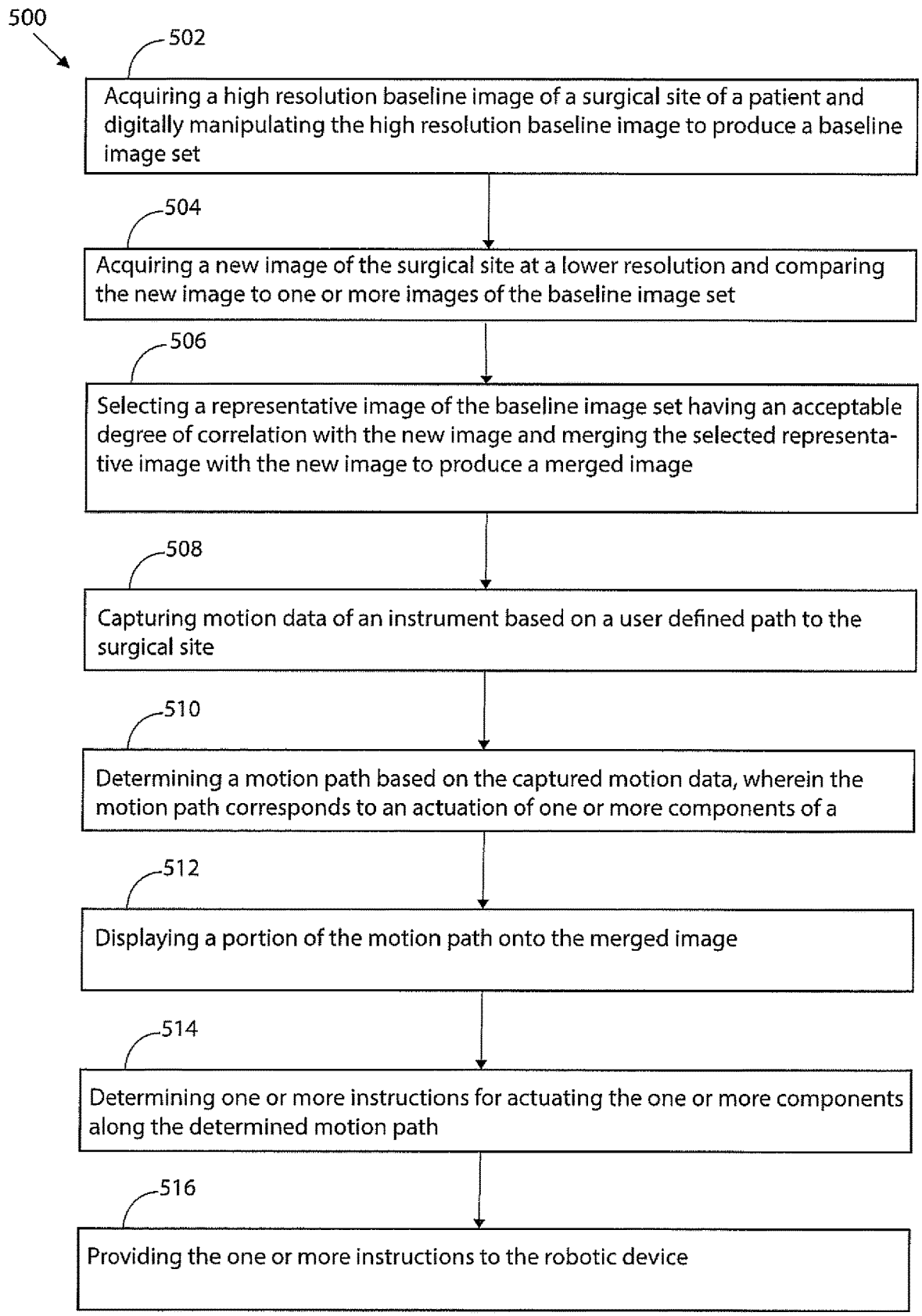
FIG. 5 illustrates a flow diagram of an example method during a surgical procedure, according to an embodiment of the present disclosure.

Referring to FIG. 5, an example method 500 during a surgical procedure may include one or more operations, functions, or actions as illustrated by blocks 502-516. In one embodiment, the method 500 is implemented in whole or in part by the system 100 of FIG. 1.

As shown by block 502, the method 500 includes acquiring a high resolution baseline image of a surgical site of a patient and digitally manipulating the high resolution baseline image to produce a baseline image set.

In one example, the image processing device 122 is configured to provide high quality real-time images on the displays 123, 124 that are derived from lower detail images obtained using lower doses of radiation. A lower dose image is too "noisy" and does not provide enough information about the local anatomy for accurate image guided surgery. While the full dose image provides a crisp view of the surgical site, the higher radiation dose makes taking multiple full dose images during a procedure highly problematic.

In one example, a baseline high resolution full dose image is acquired of the surgical site and stored in a memory associated with the image processing device 122. In some cases where the C-arm is moved during the procedure, multiple high resolution images can be obtained at different locations in the surgical site, and then these multiple images "stitched" together to form a composite base image. Movement of the C-arm, and more particularly "tracking" the acquired image during these movements, is accounted for in other steps described in more detail herein. For the present discussion it is assumed that the imaging system is relative fixed, meaning that only very limited movement of the C-arm and/or patient are contemplated, such as might arise in an epidural pain procedure, spinal K-wire placement or stone extraction. In one scenario, the baseline image is projected on the display 123 for verification that the surgical site is properly centered within the image.

In some cases, new full dose images may be obtained until a suitable baseline image is obtained. In procedures in which the C-arm is moved, new baseline images are obtained at the new location of the imaging device, as discussed below. If the displayed image is acceptable as a baseline image, a button may be depressed on a user interface, such as on the display device 126 or interface 125. In procedures performed on anatomical regions where a substantial amount of motion due to physiological processes (such as respiration) is expected, multiple baseline images may be acquired for the same region over multiple phases of the cycle. These images may be tagged to temporal data from other medical instruments, such as an ECG or pulse oximeter.

Once the baseline image is acquired, a baseline image set is generated in which the original baseline image is digitally rotated, translated and resized to create thousands of permutations of the original baseline image. For instance, a typical two dimensional (2D) image of 128.times.128 pixels may be translated .+−0.15 pixels in the x and y directions at 1 pixel intervals, rotated .+−0.9.degree. at 3.degree. intervals and scaled from 92.5% to 107.5% at 2.5% intervals (4 degrees of freedom, 4D), yielding 47,089 images in the baseline image set. A three-dimensional (3D) image will imply a 6D solution space due to the addition of two additional rotations orthogonal to the x and y axis. An original computed tomography (CT) image data set can be used to form many thousands of digitally reconstructed radiographs (DRRs) in a similar fashion. Thus, in this step, the original baseline image spawns thousands of new image representations as if the original baseline image was acquired at each of the different movement permutations. This "solution space" may be stored in a graphics card memory, such as in the graphics processing unit (GPU) of the image processing device 122, or formed as a new image which is then sent to the GPU, depending on the number of images in the solution space and the speed at which the GPU can produce those images. With current computing power, on a free standing, medical grade computer, the generation of a baseline image set having nearly 850,000 images can occur in less than one second in a GPU because the multiple processors of the GPU can each simultaneously process an image.

As shown by block 504, the method 500 includes acquiring a new image of the surgical site at lower resolution and comparing the new image to one or more images of the baseline image set. In one example, a low dose image is acquired via the C-Arm 103 and stored in the memory associated with the image processing device 122, and projected on display 123. Since the new image is obtained at a lower dose of radiation it is very noisy. Therefore, the new image may be merged with an image from the baseline image set to produce a clearer image on the second display 124 that conveys more useful information to the surgeon. In one example, merging the images may be accomplished through an image recognition or registration step in which the new image is compared to the images in the baseline image set to find a statistically meaningful match. Continuing with this example, a new "merged" image is generated and may be displayed on display 124 adjacent the view of the original new image. At various times throughout a surgical procedure, a new baseline image may be obtained that is used to generate a new baseline image set.

As shown by block 506, the method 500 includes selecting a representative image of the baseline image set having an acceptable degree of correlation with the new image and merging the selected representative image with the new image to produce a merged image. In one example, selecting a representative image of the baseline image set includes comparing the current new image to the images in the baseline image set. Since this step occurs during the surgical procedure, time and accuracy are critical. Preferably, the step can obtain an image registration in less than one second so that there is no meaningful delay between when the image is taken by the C-arm and when the merged image is displayed on the device 126. Various algorithms may be employed that may be dependent on various factors, such as the number of images in the baseline image set, the size and speed of the computer processor or graphics processor performing the algorithm calculations, the time allotted to perform the computations, and the size of the images being compared (e.g., 128.times.128 pixels, 1024.times.1024 pixels, etc). In one approach, comparisons are made between pixels at predetermined locations described above in a grid pattern throughout 4D space. In another heuristic approach, pixel comparisons can be concentrated in regions of the images believed to provide a greater likelihood of a relevant match. These regions may be "pre-seeded" based on knowledge from a grid or PCA search (defined below), data from a tracking system (such as an optical surgical navigation device), or location data from the DICOM file or the equivalent. Alternatively, a user can specify one or more regions of the image for comparison by marking on the baseline image the anatomical features considered to be relevant to the procedure. With this input each pixel in the region can be assigned a relevance score between 0 and 1 which scales the pixel's contribution to the image similarity function when a new image is compared to the baseline image. The relevance score may be calibrated to identify region(s) to be concentrated on or region(s) to be ignored.

In another approach, a principal component analysis (PCA) is performed, which can allow for comparison to a larger number of larger images in the allotted amount of time than is permitted with the full resolution grid approach. In the PCA approach, a determination is made as to how each pixel of the image set co-varies with each other. A covariance matrix may be generated using only a small portion of the total solution set—for instance, a randomly selected 10% of the baseline image set. Each image from the baseline image set is converted to a column vector.

In one example, a 70.times.40 pixel image becomes a 2800.times.1 vector. These column vectors are normalized to a mean of 0 and a variance of 1 and combined into a larger matrix. The covariance matrix is determined from this larger matrix and the largest eigenvectors are selected. For this particular example, it has been found that 30 PCA vectors can explain about 80% of the variance of the respective images. Thus, each 2800.times.1 image vector can be multiplied by a 2800.times.30 PCA vector to yield a 1.times.30 vector. The same steps are applied to the new image—the new image is converted to a 2800.times.1 image vector and multiplication with the 2800.times.30 PCA vector produces a 1.times.30 vector corresponding to the new image. The solution set (baseline image) vectors and the new image vector are normalized and the dot product of the new image vector to each vector in the solution space is calculated. The solution space baseline image vector that yields the largest dot product (i.e., closest to 1) is determined to be the closest image to the new image. It is understood that the present example may be altered with different image sizes and/or different principal components used for the analysis. It is further understood that other known techniques may be implemented that may utilize eigenvectors, singular value determination, mean squared error, mean absolute error, and edge detection, for instance. It is further contemplated that various image recognition approaches can be applied to selected regions of the images or that various statistical measures may be applied to find matches falling within a suitable confidence threshold. A confidence or correlation value may be assigned that quantifies the degree of correlation between the new image and the selected baseline image, or selected ones of the baseline image set, and this confidence value may be displayed for the surgeon's review. The surgeon can decide whether the confidence value is acceptable for the particular display and whether another image should be acquired.

In image guided surgical procedures, tools, implants and instruments will inevitably appear in the image field. These objects are typically radiodense and consequently block the relevant patient anatomy from view. The new low dose image obtained will thus include an artifact of the tool T that will not correlate to any of the baseline image set. The presence of the tool in the image thus ensures that the comparison techniques described above will not produce a high degree of registration between the new image and any of the baseline image set. Nevertheless, if the end result of each of the above procedures is to seek out the highest degree of correlation, which is statistically relevant or which exceeds a certain threshold, the image registration may be conducted with the entire new low dose image, tool artifact and all.

Alternatively, the image registration steps may be modified to account for the tool artifacts on the new image. In one approach, the new low dose image may be evaluated to determine the number of image pixels that are "blocked" by the tool. This evaluation can involve comparing a grayscale value for each pixel to a threshold and excluding pixels that fall outside that threshold. For instance, if the pixel grayscale values vary from 0 (completely blocked) to 10 (completely transparent), a threshold of 3 may be applied to eliminate certain pixels from evaluation. Additionally, when location data is available for various tracked tools, algorithmically areas that are blocked can be mathematically avoided.

In another approach, the image recognition or registration step may include steps to measure the similarity of the low dose image to a transformed version of the baseline image (i.e., a baseline image that has been transformed to account for movement of the C-arm) or of the patient. In an image-guided surgical procedure, the C-arm system acquires multiple X-ray images of the same anatomy. Over the course of this series of images the system may move in small increments and surgical tools may be added or removed from the field of view, even though the anatomical features may remain relatively stable. The approach described below takes advantage of this consistency in the anatomical features by using the anatomical features present in one image to fill in the missing details in another later image. This approach further allows the transfer of the high quality of a full dose image to subsequent low dose images.

In one embodiment, a similarity function in the form of a scalar function of the images is used to determine the registration between a current low dose image and a baseline image. To determine this registration it is first necessary to determine the incremental motion that has occurred between images. This motion can be described by four numbers corresponding to four degrees of freedom—scale, rotation and vertical and horizontal translation. For a given pair of images to be compared knowledge of these four numbers allows one of the images to be manipulated so that the same anatomical features appear in the same location between both images. The scalar function is a measure of this registration and may be obtained using a correlation coefficient, dot product or mean square error. By way of example, the dot product scalar function corresponds to the sum of the products of the intensity values at each pixel pair in the two images. For example, the intensity values for the pixel located at 1234, 1234 in each of the low dose and baseline images are multiplied. A similar calculation is made for every other pixel location and all of those multiplied values are added for the scalar function. It can be appreciated that when two images are in exact registration this dot product will have the maximum possible magnitude. In other words, when the best combination is found, the corresponding dot product is typically higher than the others, which may be reported as the Z score (i.e., number of standard deviations above the mean). A Z score greater than 7.5 represents a 99.9999999% certainty that the registration was not found by chance. It should be borne in mind that the registration being sought using this dot product is between a baseline image of a patient's anatomy and a real-time low dose image of that same anatomy taken at a later time after the viewing field and imaging equipment may have moved or non-anatomical objects introduced into the viewing field.

This approach is particularly suited to performance using a parallel computing architecture such as the GPU which consists of multiple processors capable of performing the same computation in parallel. Each processor of the GPU may thus be used to compute the similarity function of the low dose image and one transformed version of the baseline image. In this way, multiple transformed versions of the baseline image can be compared to the low dose image simultaneously. The transformed baseline images can be generated in advance when the baseline is acquired and then stored in GPU memory. Alternatively, a single baseline image can be stored and transformed on the fly during the comparison by reading from transformed coordinates with texture fetching. In situations in which the number of processors of the GPU greatly exceeds the number of transformations to be considered, the baseline image and the low dose image can be broken into different sections and the similarity functions for each section can be computed on different processors and then subsequently merged.

To further accelerate the determination of the best transformation to align two images, the similarity functions can first be computed with down-sampled images that contain fewer pixels. This down-sampling can be performed in advance by averaging together groups of neighboring pixels. The similarity functions for many transformations over a broad range of possible motions can be computed for the down-sampled images first. Once the best transformation from this set is determined that transformation can be used as the center for a finer grid of possible transformations applied to images with more pixels. In this way, multiple steps are used to determine the best transformation with high precision while considering a wide range of possible transformations in a short amount of time.

In order to reduce the bias to the similarity function caused by differences in the overall intensity levels in the different images, and to preferentially align anatomical features in the images that are of interest to the user, the images can be filtered before the similarity function is computed. Such filters will ideally suppress the very high spatial frequency noise associated with low dose images, while also suppressing the low spatial frequency information associated with large, flat regions that lack important anatomical details. This image filtration can be accomplished with convolution, multiplication in the Fourier domain or Butterworth filters, for example. It is thus contemplated that both the low dose image and the baseline image(s) will be filtered accordingly prior to generating the similarity function.

As previously explained, non-anatomical features may be present in the image, such as surgical tools, in which case modifications to the similarity function computation process may be necessary to ensure that only anatomical features are used to determine the alignment between low dose and baseline images. A mask image can be generated that identifies whether or not a pixel is part of an anatomical feature. In one aspect, an anatomical pixel may be assigned a value of 1 while a non-anatomical pixel is assigned a value of 0. This assignment of values allows both the baseline image and the low dose image to be multiplied by the corresponding mask images before the similarity function is computed as described above In other words, the mask image can eliminate the non-anatomical pixels to avoid any impact on the similarity function calculations.

To determine whether or not a pixel is anatomical, a variety of functions can be calculated in the neighborhood around each pixel. These functions of the neighborhood may include the standard deviation, the magnitude of the gradient, and/or the corresponding values of the pixel in the original grayscale image and in the filtered image. The "neighborhood" around a pixel includes a predetermined number of adjacent pixels, such as a 5.times.5 or a 3.times.3 grid. Additionally, these functions can be compounded, for example, by finding the standard deviation of the neighborhood of the standard deviations, or by computing a quadratic function of the standard deviation and the magnitude of the gradient. One example of a suitable function of the neighborhood is the use of edge detection techniques to distinguish between bone and metallic instruments. Metal presents a "sharper" edge than bone and this difference can be determined using standard deviation or gradient calculations in the neighborhood of an "edge" pixel. The neighborhood functions may thus determine whether a pixel is anatomic or non-anatomic based on this edge detection approach and assign a value of 1 or 0 as appropriate to the pixel.

Once a set of values has been computed for the particular pixel, the values can be compared against thresholds determined from measurements of previously-acquired images and a binary value can be assigned to the pixel based on the number of thresholds that are exceeded. Alternatively, a fractional value between 0 and 1 may be assigned to the pixel, reflecting a degree of certainty about the identity of the pixel as part of an anatomic or non-anatomic feature. These steps can be accelerated with a GPU by assigning the computations at one pixel in the image to one processor on the GPU, thereby enabling values for multiple pixels to be computed simultaneously. The masks can be manipulated to fill in and expand regions that correspond to non-anatomical features using combinations of morphological image operations such as erosion and dilation.

Once the image registration is complete, the new image may be displayed with the selected image from the baseline image set in different ways. In one approach, the two images are merged. The two images may be merged by combining the digital representation of the images in a conventional manner, such as by adding or averaging pixel data for the two images. In one embodiment, the surgeon may identify one or more specific regions of interest in the displayed image, such as through the user interface 125, and the merging operation can be configured to utilize the baseline image data for the display outside the region of interest and conduct the merging operation for the display within the region of interest. The user interface 125 may be provided with a "slider" that controls the amount the baseline image versus the new image that is displayed in the merged image. In another approach, the surgeon may alternate between the correlated baseline image and the new image or merged image. The surgeon may alternate between these views to get a clearer view of the underlying anatomy and a view of the current field with the instrumentation T, which in effect by alternating images digitally removes the instrument from the field of view, clarifying its location relative to the anatomy blocked by it.

As shown by block 508, the method 500 includes capturing motion data of an instrument based on a user defined path to the surgical site. In one example, tracking device 130 may be configured to capture one or more images of the instrument H as the instrument H is used in a surgical procedure. The captured one or more images are processed so as to determine orientation and position data associated with one or more IR markers coupled to the instrument H. The determined orientation and position data associated with the one or more IR markers is then used to determine the three-dimensional pose data of the instrument H over a given period of time. In one example, the instrument H may be placed at a known location within the operating room to indicate the trigger of capturing motion data. Continuing with this example, the processing device 122 may be configured to determine when the instrument H has not moved within a predetermined amount of time as an indicator to end the capture of motion data. In another example, a button may be depressed on a user interface, such as on the display device 126 or interface 125 to toggle between starting and stopping the capture of motion data associated with instrument H.

As shown by block 510, the method 500 also includes determining a motion path corresponding to the captured motion data, wherein the motion path is associated with actuation of one or more components of a robotic device. In one example, the motion path may include robotic movements that place an end effector of the robotic device at particular positions in space at particular points in time that correspond to the positions of the instrument H according to the captured motion data. In one example, the motion path may include a sequence of Cartesian coordinates and rotation angles indicating the position of the instrument H overtime.

Block 510 may also, or instead, include comparing a position of the one or more infrared reflectors of the portable instrument to a position of one or more infrared reflectors coupled to the patient. Block 510 may further include based on the comparison, determining a distance between the one or more infrared reflectors of the portable instrument and the one or more infrared reflectors coupled to the patient is within a safety threshold. Based on the determination, block 510 may further include determining one or more adjustments to the actuation of the one or more components of the robotic device.

As shown by block 512, the method 500 also includes displaying a portion of the motion path onto the merged image. In one example, in order to form a pilot hole for pedicle screw placement in a vertebral pedicle with the aid of the robotic device 140, the instrument H is advanced by a surgeon to the pedicle target site where the pilot hole is to be formed. In this example, the tracking device 130 is configured to capture the position and orientation of instrument H and provide the position and orientation information to the processing device 122. Continuing with this example, the processing device 122 is configured to provide an image of the surgical site for display and overlay at least a portion of the motion path on the image of the surgical site.

Figure 7:
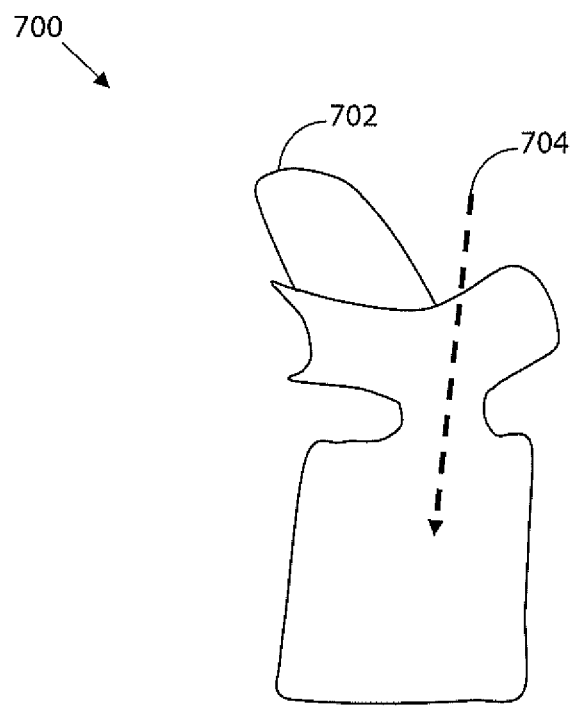
FIG. 7 illustrates an example image that may be displayed during a surgical procedure, according to an embodiment of the present disclosure.

Referring to FIG. 7, FIG. 7 illustrates an example two-dimensional merged image 700 of a surgical site that includes vertebra 702 and a portion of a motion path 704. In one example, a surgeon may position instrument H at a pedicle target site as described above and view merged image 700 to determine if the trajectory of the portion of the motion path 704 aligns with a surgical plan. In this example, based on a surgeon viewing the portion of the motion path 704 as illustrated and accepting the corresponding trajectory for forming a pilot hole, the surgeon may provide an input via the processing device 122 to use the motion path associated with image 700 for determining one or more instructions that actuate the one or more components of the robotic device along the determined motion path. The processing device 122 may then process or provide the orientation and position information of the instrument H to the robotic device 140 in order to enable the robotic device 140 to perform the movements necessary along the determined portion of the motion path 704.

Alternatively, the method 500 may include displaying a portion of the motion path onto a three-dimensional image. In one example, the processing device 122 may include computer executable instructions that are configured to perform a segmentation step. As used herein, "segmentation" describes a process that identifies individual vertebrae within three-dimensional image data so that the vertebrae can be separated and treated, manipulated, and displayed distinct from one another. The segmentation step may employ a segmentation algorithm that uses imaging processing and image recognition software to automate the spinal level segmentation process. In one embodiment, the computer executable instructions automatically identify and extract the spine curve, detect and identify each individual vertebra, until they are segmented from one another. One or more adaptive meshes may be applied to generate a segmented three-dimensional model of the spine. Each vertebra or other anatomical features can be separately colored to visibly enhance the bone-soft tissue interface, or just the margin can be colored.

Figure 8:
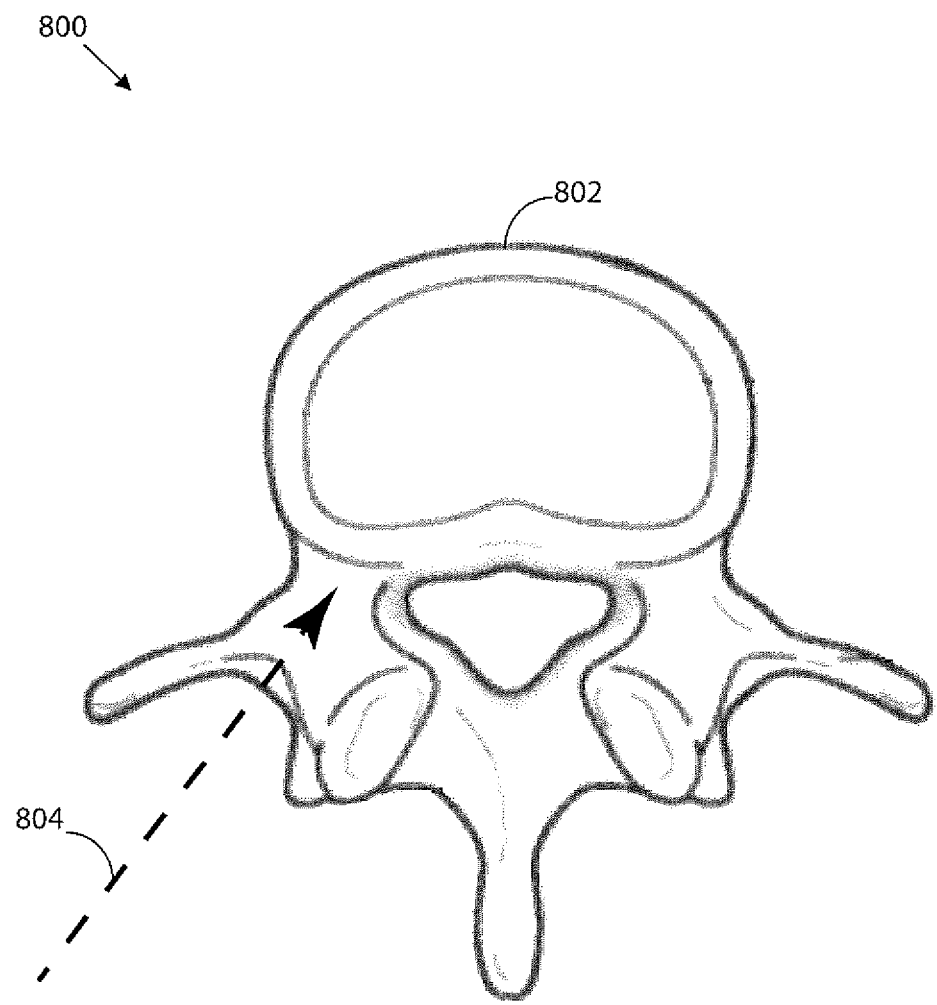
FIG. 8 illustrates another example image that may be displayed during a surgical procedure, according to an embodiment of the present disclosure.

Referring to FIG. 8, FIG. 8 illustrates an example three-dimensional image 800 that includes vertebra 802 segmented from other vertebrae and a portion of a motion path 804. In one example, a surgeon may position instrument H at a pedicle target site as described herein and view the three-dimensional image 800 to determine if the trajectory of the portion of the motion path 804 aligns with a surgical plan. In this example, based on a surgeon viewing the portion of the motion path 804 as illustrated and accepting the corresponding trajectory for forming a pilot hole, the surgeon may provide an input via the processing device 122 to use the motion path associated with image 800 for determining one or more instructions that actuate the one or more components of the robotic device along the determined motion path. The processing device 122 may then process or provide the orientation and position information of the instrument H to the robotic device 140 in order to enable the robotic device 140 to perform the movements necessary along the determined portion of the motion path 804.

Referring back to FIG. 5, as shown by block 514, the method 500 also includes determining one or more instructions for actuating the one or more components along the determined motion path. In one example, a sequence of robot joint parameters, including joint angles, velocities, and/or accelerations may be determined for the robot that locate the position and orientation of the robot's end effector over time in order to position the robot tool within space. In one example, a direct mapping between joint parameters of the robot and positions of the robot tool at particular timestamps may be determined. In one example, rather than a direct mapping, robot joint parameters may be determined in order to approximate the position of the robot tool. In one embodiment, robot movements may be modified in order to smooth motion curves of the robot and/or of the robot tool in order to avoid jerking or disconnected movements while the robot is moving the robot tool. In one example, the positions within the motion path of the robotic end effector may be scaled to account for the difference in size between the instrument H and the robotic end effector.

In one example, the one or more instructions for actuating the one or more components along the determined motion path may be refined before the robot is provided with the one or more instructions. For example, the motion path of the robot may be scaled up or down in size relative to the determined motion path of the instrument H.

As shown by block 516, the method 500 also includes providing the one or more instructions to the robotic device. In one example, the one or more instructions may be provided via a wireless or wired communication interface between the processing device 122 and the robotic device 140.

Figure 6:
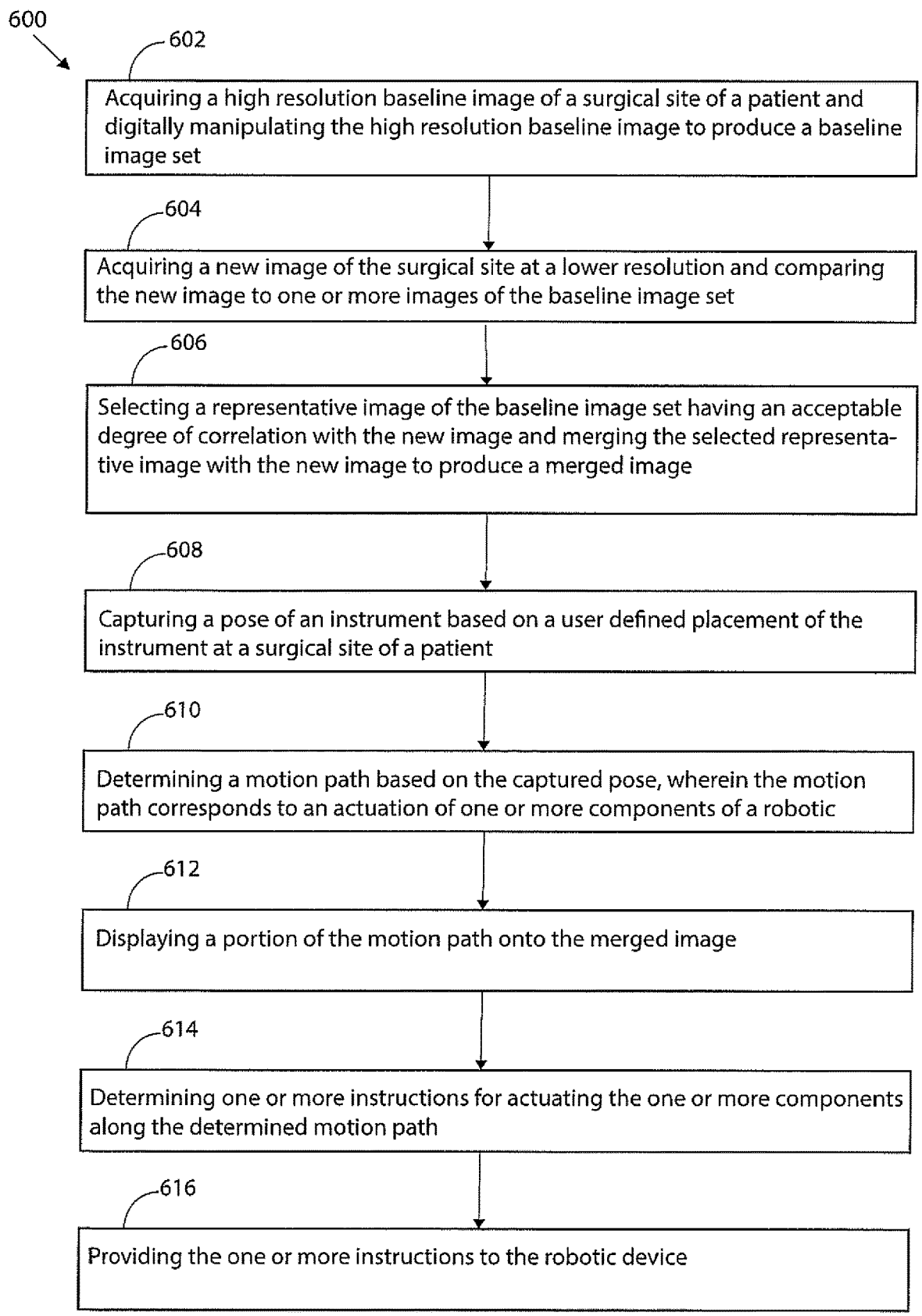
FIG. 6 illustrates another flow diagram of an example method during a surgical procedure, according to an embodiment of the present disclosure.

Referring to FIG. 6, an example method 600 during a surgical procedure may include one or more operations, functions, or actions as illustrated by blocks 602-616. In one embodiment, the method 600 is implemented in whole or in part by the system 100 of FIG. 1.

As shown by block 602, the method 600 includes acquiring a high resolution baseline image of a surgical site of a patient and digitally manipulating the high resolution baseline image to produce a baseline image set. Block 602 may be similar in functionality to block 502 of method 500.

As shown by block 604, the method 600 also includes acquiring a new image of the surgical site at lower resolution and comparing the new image to one or more images of the baseline image set. Block 604 may be similar in functionality to block 504 of method 500.

As shown by block 606, the method 600 also includes selecting a representative image of the baseline image set having an acceptable degree of correlation with the new image and merging the selected representative image with the new image to produce a merged image. Block 606 may be similar in functionality to block 506 of method 500.

As shown by block 608, the method 600 also includes capturing a pose of an instrument based on a user defined placement of the instrument at a surgical site of a patient. Block 608 may be similar in functionality to block 508 of method 500.

As shown by block 610, the method 600 also includes determining a motion path corresponding to the captured pose of the instrument, wherein the motion path is associated with actuation of one or more components of a robotic device. Block 610 may be similar in functionality to block 510 of method 500.

Block 610 may also, or instead, include comparing a position of the one or more infrared reflectors of the portable instrument to a position of one or more infrared reflectors coupled to the patient. Block 610 may further include based on the comparison, determining a distance between the one or more infrared reflectors of the portable instrument and the one or more infrared reflectors coupled to the patient is within a safety threshold. Based on the determination, block 610 may further include determining one or more adjustments to the actuation of the one or more components of the robotic device.

As shown by block 612, the method 600 also includes displaying a portion of the motion path onto the merged image. Block 612 may be similar in functionality to block 512 of method 500. Alternatively, the portion of the motion path can be displayed on a three-dimensional image of a vertebra As shown by block 614, the method 600 also includes determining one or more instructions for actuating the one or more components along the determined motion path. Block 614 may be similar in functionality to block 514 of method 500.

As shown by block 616, the method 600 also includes providing the one or more instructions to the robotic device. Block 616 may be similar in functionality to block 516 of method 500.

Figure 9:
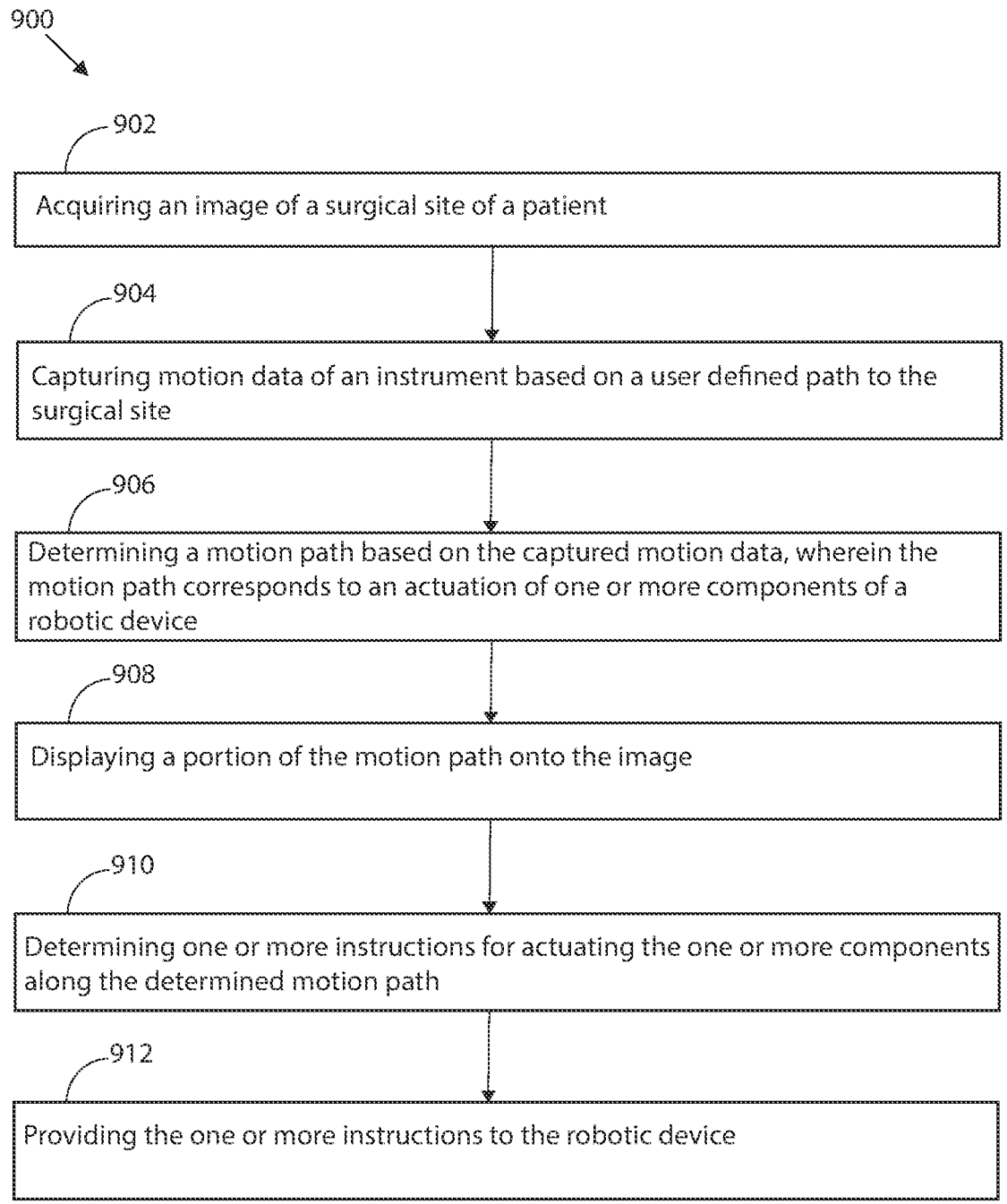
FIG. 9 illustrates another flow diagram of an example method during a surgical procedure, according to an embodiment of the present disclosure.

Referring to FIG. 9, an example method 900 during a surgical procedure may include one or more operations, functions, or actions as illustrated by blocks 902-912. In one embodiment, the method 900 is implemented in whole or in part by the system 100 of FIG. 1.

As shown by block 902, the method 900 includes acquiring an image of a surgical site of a patient. In one example, the image of the surgical site may be a two-dimensional image. In another example, a three-dimensional image data set of the patient's anatomy is loaded into the system prior to the surgical procedure. This image data set may be a pre-operative CT scan, a pre-operative MRI, or an intraoperative three-dimensional image data set acquired from an intraoperative imager. In one scenario, the three-dimensional image data set is uploaded to the image processing device 122 and converted to series of DRRs to approximate all possible two-dimensional C-Arm images that could be acquired, thus serving as a baseline for comparison and matching intraoperative two-dimensional images.

As shown by block 904, the method 900 also includes capturing motion data of an instrument based on a user defined path to the surgical site. Block 904 may be similar in functionality to block 508 of method 500.

As shown by block 906, the method 900 also includes determining a motion path corresponding to the captured motion data, wherein the motion path is associated with actuation of one or more components of a robotic device. Block 906 may be similar in functionality to block 510 of method 500.

As shown by block 908, the method 900 also includes displaying a portion of the motion path onto the merged image. Block 908 may be similar in functionality to block 512 of method 500.

As shown by block 910, the method 900 also includes determining one or more instructions for actuating the one or more components along the determined motion path. Block 910 may be similar in functionality to block 514 of method 500.

As shown by block 912, the method 900 also includes providing the one or more instructions to the robotic device. Block 912 may be similar in functionality to block 516 of method 500.

Figure 10:
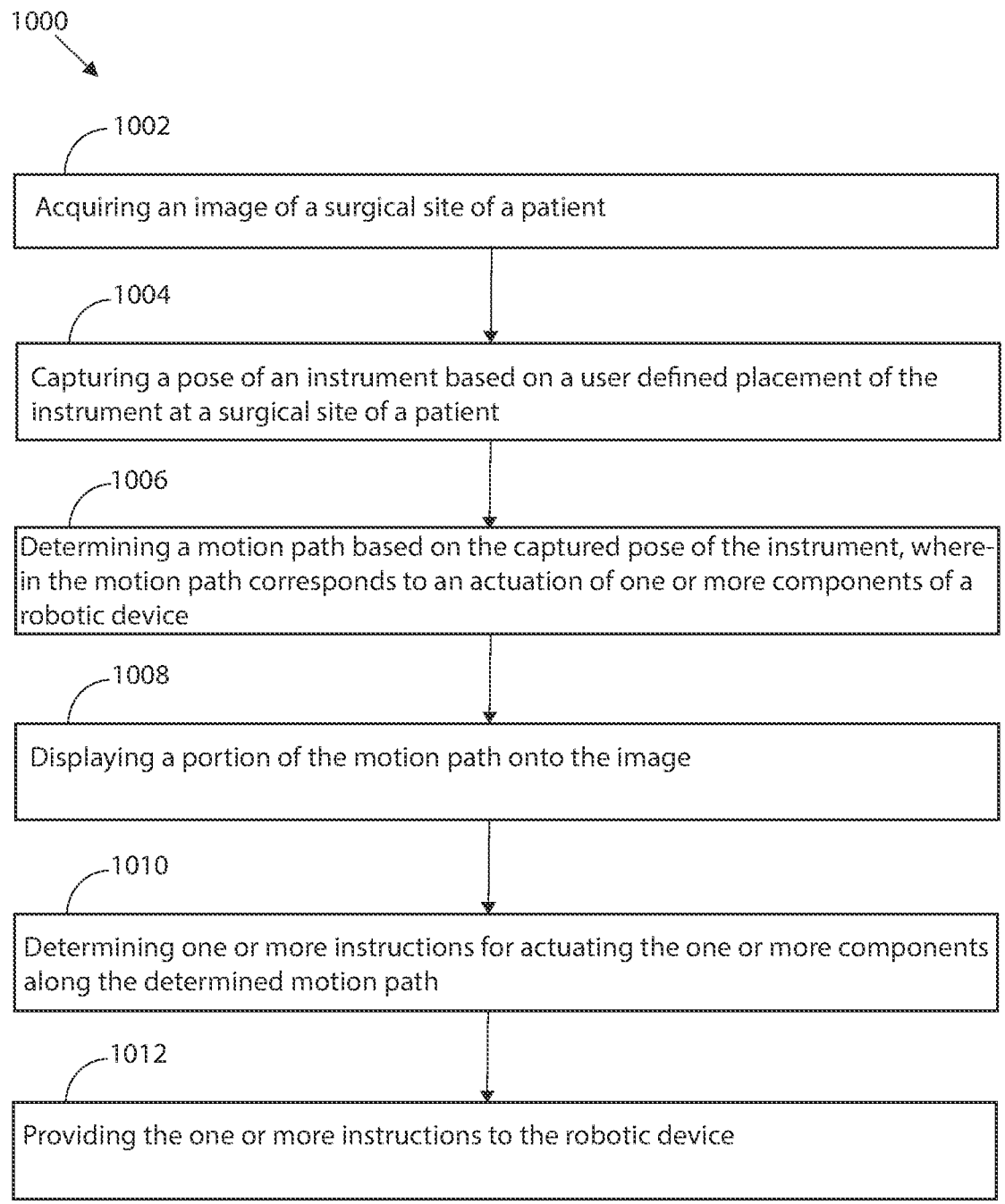
FIG. 10 illustrates another flow diagram of an example method during a surgical procedure, according to an embodiment of the present disclosure.

Referring to FIG. 10, an example method 1000 during a surgical procedure may include one or more operations, functions, or actions as illustrated by blocks 1002-1012. In one embodiment, the method 900 is implemented in whole or in part by the system 100 of FIG. 1.

As shown by block 1002, the method 1000 includes acquiring an image of a surgical site of a patient. Block 1002 may be similar in functionality to block 902 of method 900.

As shown by block 1004, the method 1000 also includes capturing a pose of an instrument based on a user defined placement of the instrument at a surgical site of a patient. Block 1004 may be similar in functionality to block 508 of method 500.

As shown by block 1006, the method 1000 also includes determining a motion path corresponding to the captured pose of the instrument, wherein the motion path is associated with actuation of one or more components of a robotic device. Block 1006 may be similar in functionality to block 510 of method 500.

As shown by block 1008, the method 1000 also includes displaying a portion of the motion path onto the merged image. Block 1008 may be similar in functionality to block 512 of method 500.

As shown by block 1010, the method 1000 also includes determining one or more instructions for actuating the one or more components along the determined motion path. Block 1010 may be similar in functionality to block 514 of method 500.

As shown by block 1012, the method 1000 also includes providing the one or more instructions to the robotic device. Block 1012 may be similar in functionality to block 516 of method 500.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

What is claimed is:

1. A method comprising:
acquiring an image of a surgical site of a patient;
determining motion data of an instrument based on a user defined path to the surgical site;
determining, based on the motion data, a motion path of a robotic device;
displaying a portion of the motion path onto at least a portion of the image;
determining one or more instructions for actuating the one or more components to cause the robotic device to move according to the motion path; and
providing the one or more instructions to the robotic device.

2. The method of claim 1, wherein the image of the surgical site is a three-dimensional image.

3. The method of claim 1, wherein determining the motion data includes:
capturing, with a tracking device, one or more images of the instrument or markers coupled to the instrument; and
processing the one or more images to determine the motion data.

4. The method of claim 1, wherein the method further comprises:
obtaining a predetermined trajectory;
determining one or more additional instructions for actuating the one or more components to align a trajectory of the robotic device with the predetermined trajectory; and
providing the one or more additional instructions to the robotic device.

5. The method of claim 1, further comprising:
after displaying the portion of the motion path onto the image, receiving approval input,
wherein the determining of the one or more instructions for actuating the one or more components is based on the received approval input.

6. The method of claim 1, further comprising:
determining a score associated with the motion path; and
selecting a visual effect based on the score,
wherein the displaying of the portion of the motion path onto the image is based on the visual effect.

7. The method of claim 6,
wherein the score corresponds to a likelihood of pedicle breach.

8. The method of claim 6,
wherein the visual effect is a blinking effect or a color.

9. The method of claim 6,
actuating the robotic device according to the provided one or more instructions.

10. The method of claim 1, further comprising:
determining that the motion path intersects with one or more predetermined boundaries within the surgical site; and
responsive to determining that the motion path intersects with the one or more predetermined boundaries, selecting a visual effect for the motion path, wherein the displaying of the portion of the motion path onto the image is based on the visual effect.

11. The method of claim 1, wherein the instrument is mounted to the robotic device.

12. The method of claim 1, wherein the instrument is a handheld instrument.

13. A method comprising:
acquiring a three-dimensional image of a surgical site of a patient;
capturing a pose of an instrument based on a user defined placement of the instrument at a surgical site of a patient;
determining a motion path for a robotic device that corresponds to the captured pose of the instrument;
displaying a portion of the motion path onto the three-dimensional image;
determining one or more instructions for actuating one or more components of the robotic device to cause at least a portion of the robotic device to move the along the motion path; and
providing the one or more instructions to the robotic device.

14. The method of claim 13, further comprising:
causing a manipulator of the robotic device to move toward the surgical site along the motion path; and
causing the manipulator of the robotic device to move away from the surgical site along the motion path.

15. The method of claim 13, further comprising:
receiving an input confirming that the motion path aligns with a surgical operative plan,
wherein the providing or determining the one or more instructions is responsive to receiving the input.

16. The method of claim 13, further comprising:
determining that the motion path intersects with one or more predetermined boundaries within the surgical site; and
causing display of a visual effect responsive to determining that the motion path intersects with one or more predetermined boundaries within the surgical site.

17. A system comprising:
a tracking device;
a robotic device; and
a processing device comprising:
a processor; and
a non-transitory computer readable medium having stored thereon instructions that, when executed by the processor, cause the system to:
receive an image of a surgical site of a patient;
capturing, via the tracking device, a pose of an instrument based on a user defined placement of the instrument at a surgical site of a patient;
determine, by the processor, a motion path corresponding to the captured pose of the instrument, wherein the motion path is associated with actuation of one or more components of the robotic device;
provide instructions to display a portion of the motion path onto the image;
determine, by the processor, one or more instructions for actuating the one or more components along the determined motion path; and
provide the one or more instructions to the robotic device.

18. The system of claim 17, wherein the image of the surgical site is a three-dimensional image.

19. The system of claim 17, wherein the non-transitory computer readable medium having stored thereon instructions that, when executed by the processor, cause the system to provide the one or more instructions to the robotic device further comprises instructions to:
receive an input confirming that the portion of the determined motion path aligns with a surgical operative plan.

20. The system of claim 17, wherein the non-transitory computer readable medium having stored thereon instructions that, when executed by the processor, further cause the system to:
determine that the motion path intersects with one or more predetermined boundaries within the surgical site; and
provide for display a varying visual effect of the motion path.

* * * * *